(12) United States Patent
Mandla et al.

(10) Patent No.: US 11,766,469 B2
(45) Date of Patent: Sep. 26, 2023

(54) Q-PEPTIDE HYDROGEL PROMOTES IMMUNE MODULATION AND MACROPHAGE DIFFERENTIATION

(71) Applicant: Quthero, Inc., Miami, FL (US)

(72) Inventors: Serena Mandla, Toronto (CA); Milica Radisic, Toronto (CA)

(73) Assignee: QUTHERO, INC., Miami, FL (US)

(*) Notice: Subject to any disclaimer, the term of this patent is extended or adjusted under 35 U.S.C. 154(b) by 153 days.

(21) Appl. No.: 17/086,786

(22) Filed: Nov. 2, 2020

(65) Prior Publication Data

US 2021/0128688 A1 May 6, 2021

Related U.S. Application Data

(60) Provisional application No. 62/930,122, filed on Nov. 4, 2019.

(51) Int. Cl.

| | | |
|---|---|---|
| *A61K 38/08* | (2019.01) | |
| *A61K 38/16* | (2006.01) | |
| *A61K 38/00* | (2006.01) | |
| *A61P 17/02* | (2006.01) | |
| *A61F 13/00* | (2006.01) | |
| *A61K 9/70* | (2006.01) | |
| *A61K 9/14* | (2006.01) | |
| *A61K 38/18* | (2006.01) | |
| *C12N 5/077* | (2010.01) | |
| *A61K 47/61* | (2017.01) | |
| *A61K 9/06* | (2006.01) | |
| *G01N 33/68* | (2006.01) | |
| *A61K 47/42* | (2017.01) | |

(52) U.S. Cl.
CPC ............ *A61K 38/1891* (2013.01); *A61K 9/06* (2013.01); *A61K 9/14* (2013.01); *A61K 9/70* (2013.01); *A61K 9/7007* (2013.01); *A61K 9/7015* (2013.01); *A61K 38/08* (2013.01); *A61K 47/42* (2013.01); *A61K 47/61* (2017.08); *A61P 17/02* (2018.01); *C12N 5/0669* (2013.01); *G01N 33/6893* (2013.01); *C12N 2501/17* (2013.01)

(58) Field of Classification Search
None
See application file for complete search history.

(56) References Cited

U.S. PATENT DOCUMENTS 9,096,643 B2 * 8/2015 Radisic ............... C12N 5/0068
2019/0328824 A1 * 10/2019 Radisic ............... A61K 38/08

OTHER PUBLICATIONS

Mandla et al., ACS Biomater. Sci. Eng. 5:4542-4550 (first available Jul. 2019) (Year: 2019).*
Krzyszczyk et al., Front. Physiol. 9:22 pages (2018) (Year: 2018).*

* cited by examiner

*Primary Examiner* — Thea D' Ambrosio
(74) *Attorney, Agent, or Firm* — Ridout & Maybee LLP

(57) ABSTRACT

The present invention examines the interaction between an angiopoietin-1 mimetic peptide, QHREDGS (glutamine-histidine-arginine-glutamic acid-aspartic acid-glycine-serine (SEQ ID NO: 1)) immobilized to a collagen-chitosan hydrogel, and murine bone marrow derived macrophages. When macrophages were cultured in the presence of the peptide conjugated to a hydrogel, both pro-inflammatory and anti-inflammatory cytokines were produced, in contrast to the application of soluble peptide which elicited minimal cytokine secretion. This indicates a unique macrophage polarization with covalently immobilized peptide hydrogels, which can be beneficial in the context of the wound microenvironment.

13 Claims, 11 Drawing Sheets

Specification includes a Sequence Listing.

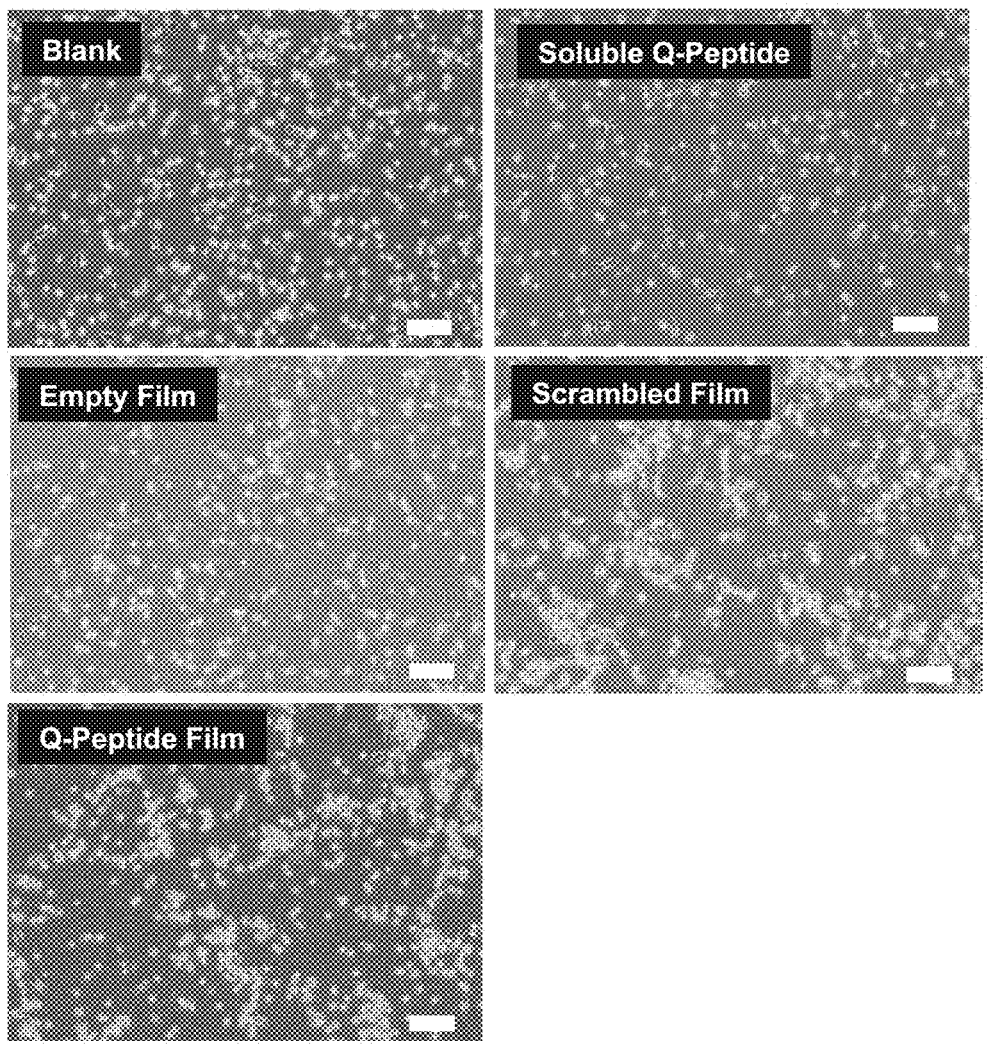
FIG.2A
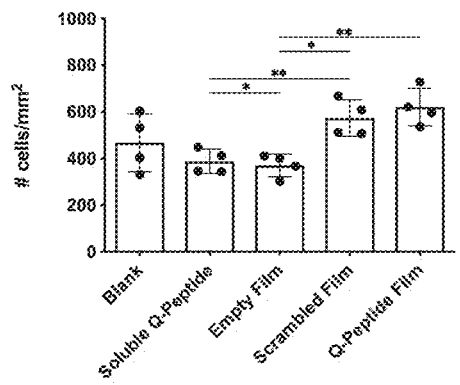
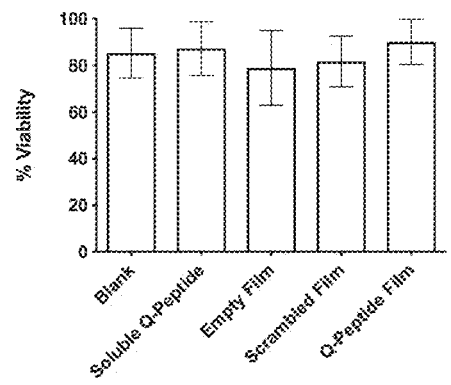
FIG.2B                FIG.2C

Q-PEPTIDE HYDROGEL PROMOTES IMMUNE MODULATION AND MACROPHAGE DIFFERENTIATION

RELATED APPLICATIONS

This application claims priority to and the benefit of U.S. Provisional Patent Application No. 62/930,122, filed on Nov. 4, 2019, the disclosure of which is hereby incorporated by reference in its entirety.

FIELD OF THE INVENTION

The invention relates to compositions, formulations and methods of use thereof, e.g., for (a) modulating the polarization state of a macrophage and (b) wound healing.

INCORPORATION-BY-REFERENCE OF SEQUENCE LISTING

The contents of the file named "QUTH-003_01US_SequenceListing_ST25", which was created on Oct. 22, 2020, and is 4 KB in size are hereby incorporated by reference in their entirety.

BACKGROUND OF THE INVENTION

Wound healing is a complex process dependent on the spatial and temporal recruitment of a number of different cells and cytokines. The immune system plays a key role in the process of wound healing, as the presence of cells such as neutrophils and macrophages contributes to the removal of any foreign pathogens, releasing cytokines necessary for cell signalling. A deregulation within any phase of this process, and more notably, the inflammatory phase, results in non-healing chronic wounds, which are not only a significant burden on the healthcare system but result in a significant decrease in patient quality of life. In fact, chronic, or non-healing wounds are typically characterized by prolonged inflammation.

Immediately following injury, the wound site is in an inflammatory phase, characterized by the presence of neutrophils and macrophages. When macrophages are recruited to the wound site, they become activated and exhibit a spectrum of polarization states, necessary in the progression of wound healing. Inflammatory response is initially required to fight infection at the wound site and initiate angiogenesis. Initially following injury, macrophages are polarized towards a pro-inflammatory, or M1 polarization phenotype. In vitro, this phenotype can be induced by interferon gamma (IFN-γ) alone or in conjunction with lipopolysaccharide (LPS; M(LPS)). Pro-inflammatory macrophages produce cytokines such as interleukin 1 beta (IL-1β, interleukin 6 (IL-6) and tumor necrosis factor alpha (TNF-α), and other effector molecules, such as reactive oxygen species and nitrogen intermediates.

In healthy wound healing, macrophages will typically undergo a shift in polarization state towards a pro-healing, anti-inflammatory, M2 macrophage after 1-3 days of acute inflammation. Anti-inflammatory macrophages can be induced in vitro with IL-4 (M(IL-4)) and IL-13, and produce cytokines, such as IL-1ra and IL-10. In reality however, macrophage polarization exists as a spectrum, in which macrophages have been able to simultaneously release cytokines associated with both pro- and anti-inflammatory responses. Several studies have demonstrated the importance of this transition in the progression of wound healing. For instance, Badylak et al. showed that the presence of pro-inflammatory macrophages was associated with long-term inflammation and scar tissue formation, while an anti-inflammatory response was associated with organized tissue remodeling and absence of persistent inflammation. Given the crucial role of macrophages in wound healing, biomaterials should be designed to provide cues to guide macrophage polarization and constructively minimize inflammatory response while promoting tissue remodeling.

Current approaches to wound healing are focused on the development of bioactive materials which interact with the tissue microenvironment to actively target cells to accelerate the healing process. Antimicrobial proteins, metals or naturally derived materials are commonly included in wound dressings as a strategy to combat wound infection in chronic wounds. Additionally, the incorporation of growth factors, such as fibroblast growth factor (FGF) and platelet derived growth factor (PDGF), has shown promise by directly mediating key cellular processes during wound healing.

SUMMARY OF INVENTION

One aspect of the present disclosure relates to a method of inducing a polarization state of a macrophage, the method comprising contacting the macrophage with a formulation, wherein the formulation comprises a peptide that comprises the amino acid sequence QHREDGS (SEQ ID NO: 1).

In some embodiments, the polarization state is characterized by an increase in release of a pro-inflammatory cytokine and an increase in anti-inflammatory cytokine production by the macrophage relative to a macrophage that has not been contacted with the formulation.

In some embodiments, the pro-inflammatory cytokine is selected from IFN-γ, IL-1β, GM-CSF, IL-6, IL-12, MCP-1, TNF-α, and a combination thereof.

In some embodiments, the anti-inflammatory cytokine is selected from IL-4, IL-10, TGF-β, and a combination thereof.

In some embodiments, the polarization state is further characterized by an increase in the ratio of TGF-β3/TGF-β1 released by the macrophage relative to a macrophage that has not been contacted with the formulation.

In some embodiments, the polarization state is characterized by an increase in expression level of CD86 and a decrease in expression level of CD206 on the macrophage relative to a macrophage that has not been contacted with the formulation.

In some embodiments, the contacting step is performed in vitro.

In some embodiments, the contacting step is performed in vivo.

In some embodiments, the contacting step is performed on a human.

In some embodiments, the formulation further comprises a carrier.

In some embodiments, the carrier is selected from hydrogel, glycerol, propylene glycol, chitosan, alginate, agarose, polyether, polyester, methylcellulose, hyaluronan, collagen, laminin, Matrigel®, fibronectin, vitronectin, poly-1-lysine, a proteoglycan, fibrin glue, a gel made by decellularization of an engineered or natural tissue, polyglycolic acid (PGA), polylactic acid (PLA), a combination of PGA and PLA such as PLGA, poly ε-caprolactone, polyvinyl alcohol (PVA), polyethylene glycol (PEG), methyl methacrylate, poly(m-ethyl methacrylate) (PMMA), poly(2-hydroxyethyl methacrylate) (PolyHEMA), poly(glycerol sebacate), a self-assembling peptide hydrogel, AcN- RARADADARARADADA-CNH (SEQ ID NO: 2), polyurethane, poly(isopropylacrylamide), poly(N-isopropylacrylamide), and a combination thereof.

In some embodiments, the peptide is conjugated to the carrier.

In some embodiments, the formulation is a hydrogel.

In some embodiments, the formulation is in the form of a gel, a tincture, a cream, an ointment, a lotion, or an aerosol spray.

In some embodiments, the formulation is delivered on a patch or a bandage.

Another aspect of the present disclosure relates to a method of modulating a polarization state of a macrophage from a subject, the method comprising: (a) contacting the macrophage with a formulation comprising an angiopoietin-1 mimetic peptide; (b) measuring expression levels of a pro-inflammatory marker and an anti-inflammatory biomarker and/or release of a pro-inflammatory cytokine and an anti-inflammatory cytokine by the macrophage in response to the contacting step; and (c) determining the polarization state after the contacting step based on a result obtained from the measuring step.

In some embodiments, the measuring step comprises measuring a change in the expression levels of the pro-inflammatory marker and the anti-inflammatory marker by the macrophage relative to a macrophage that has not been contacted with the formulation.

In some embodiments, the measuring step comprises measuring a change in release of the pro-inflammatory cytokine and an anti-inflammatory cytokine by the macrophage relative to a macrophage that has not been contacted with the formulation.

In some embodiments, the pro-inflammatory marker is CD86.

In some embodiments, the anti-inflammatory marker is CD206.

In some embodiments, the pro-inflammatory cytokine is selected from IFN-γ, IL-1β, GM-CSF, IL-6, IL-12, MCP-1, TNF-α, and a combination thereof.

In some embodiments, the anti-inflammatory cytokine is selected from IL-4, IL-10, TGF-β, and a combination thereof.

In some embodiments, the method further comprises administering the formulation to a subject in need thereof to mediate wound healing, when the polarization state after the contacting step is characterized by one or more of the following changes by the macrophage relative to a macrophage that has not been contacted with the formulation: (a) an increase in release of the pro-inflammatory cytokine and the anti-inflammatory cytokine by the macrophage; (b) an increase in the ratio of TGF-β3/TGF-β1 released by the macrophage; and/or (c) an increase in expression level of CD86 and a decrease in expression level of CD206 on the macrophage.

In some embodiments, the angiopoietin-1 mimetic peptide comprises the amino acid sequence QHREDGS (SEQ ID NO: 1).

In some embodiments, the formulation further comprises a carrier.

In some embodiments, the peptide is conjugated to the carrier.

In some embodiments, the subject is a human.

BRIEF DESCRIPTION OF THE DRAWINGS

FIG. 1A shows a schematic illustrating the delivery of the Q-Peptide hydrogel as either an extrudable gel, or a pre-gelled patch. FIG. 1B shows an image of the extruded product of the thermally crosslinked hydrogel, the EDC/NHS crosslinked hydrogel, and Duoderm, an FDA-approved control. Scale bar=1 cm. FIG. 1C demonstrates the patch format of the Q-Peptide hydrogel illustrating the i) PDMS mold used to create the patch on Tegaderm, and ii) the fully formed patch. Scale bar=1 cm. FIG. 1D shows in vitro degradation of the hydrogel with collagenase, lysozyme and PBS (n=3). Data are presented as mean ±SD. *P<0.05 compared to all groups. #P<0.05 for collagenase vs PBS and lysozyme vs PBS.

FIGS. 2A-2C show bone marrow derived macrophages (BMDMs) are not affected when cultured on the Q-Peptide hydrogel film. FIG. 2A show BMDMs cultured with blank media, soluble Q-Peptide, empty collagen-chitosan film, scrambled Q-Peptide film, and Q-Peptide film. Scale bars=250 μm. FIG. 2B shows quantification of the number of adhered cells/mm2 (n=4). FIG. 2C shows the viability of the BMDMs as assessed by fixable Zombie Violet stain. Data are presented as mean±SD. *P<0.05, ** p<0.01.

FIG. 3C shows quantification of the median fluorescence intensity for CD86. FIG. 3D shows quantification of the median fluorescence intensity for CD206. (n=3). Data are presented as mean±SD. *P<0.05, ** p<0.01.

FIG. 6A shows the total number of cells after 24 hours of culture as determined by counting adherent cells and cells in suspension. FIG. 6B shows macrophage purity following differentiation for 7 days with M-CSF and polarization. Data are presented as mean±SD.

In FIG. 8A, Zombie Violet FMO controls. Black dash: Fully stained, Solid Black: FMO-Zombie Violet, Black dot: Unstained. In FIG. 8B, F4/80 and CD11b FMO controls. Grey Dash: FMO Boundaries Black dash: Unstained boundaries. In FIG. 8C, CD206 and CD86 FMO controls. Grey Dash: FMO Boundaries Black dash: Unstained boundaries. Grey dashed lines are the gating strategy informed by the FMO staining.

DETAILED DESCRIPTION OF THE INVENTION

Figure 1A:
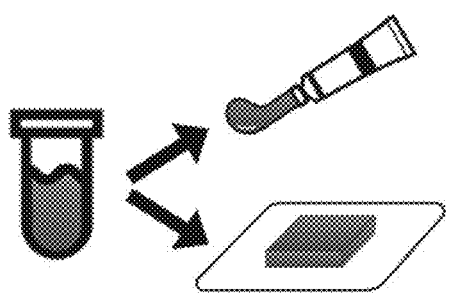
FIGS. 1A-1D show the development of the QHREDGS (Q-Peptide) conjugated to the hydrogel and the stability of the Q-Peptide hydrogel.

The present disclosure provides compositions and methods for their use. In one embodiment, the composition provides a use in modulating the polarization state of a macrophage. In one embodiment, the composition provides a use in wound healing.

I. Definitions

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of".

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "substantially," "approximately," and "about" used throughout the specification and the claims mean plus or minus 10% of the value stated, e.g., about 100 would include 90 to 110.

The term "increase" or the related term "increased" used throughout the specification and the claims means at least about 5% greater, at least about 10% greater, at least about 15% greater, at least about 20% greater, at least about 30% greater, at least about 40% greater, at least about 50% greater, at least about 60% greater, at least about 70% greater, at least about 80% greater, at least about 100% greater, at least about 120% greater, at least about 140% greater, at least about 160% greater, at least about 180% greater, or at least about 200% greater than a reference level.

The term "decrease" or the related terms "decreased," "reduce" or "reduced" used throughout the specification and the claims means at least about 5% less, at least about 10% less, at least about 15% less, at least about 20% less, at least about 30% less, at least about 40% less, at least about 50% less, at least about 60% less, at least about 70% less, at least about 80% less, or at least about 90% less than a reference level.

The term "patient" or "subject" is used throughout the specification and the claims to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat, a mammal such as mice, rats, and non-human primates, or a farm animal such as a horse, cow, sheep, etc. In general, in the present disclosure, the term patient refers to a human patient unless otherwise stated or implied from the context of the use of the term.

The terms "treat," treatment," and "treating" refer to (1) a reduction in severity or duration of a disease or condition, (2) the amelioration of one or more symptoms associated with a disease or condition without necessarily curing the disease or condition, or (3) the prevention of a disease or condition.

The terms "healing," as in "wound healing" refers to (1) a reduction in size, severity or duration of a wound, (2) the amelioration of one or more symptoms associated with a wound without necessarily curing the wound, or (3) a lessening in the growth or severity of a wound.

The term "scarless" refers to healing with no scar tissue or healing with diminished scar formation.

The term "effective" is used to describe an amount of a compound, composition or formulation which, when used within the context of its intended use, effects an intended result. The term "effective" subsumes all other effective amount or effective concentration terms, which are otherwise described or used in the present application.

II. Compositions of the Disclosure

The present disclosure provides a peptide comprising, consisting essentially of, or consisting of an amino acid sequence of $X_1X_2X_3X_4X_5X_6X_7$ (SEQ ID NO: 21), wherein $X_1$ is an optional residue selected from glutamine, threonine, serine or asparagine;
$X_2$ is an optional positively charged residue selected from histidine, arginine or lysine;
$X_3$ is glutamate, threonine, isoleucine, histidine, lysine, glutamine, tyrosine, valine or leucine;
$X_4$ is glycine or valine;
$X_5$ is an optional residue selected from serine, threonine, aspartic acid, isoleucine or glycine;
$X_6$ is an optional residue selected from leucine, valine, glutamine, glycine, isoleucine or serine;
and $X_7$ is an optional residue selected from aspartic acid, asparagine, valine or lysine.

In some embodiments, the peptide comprises, consists essentially of, or consists of an amino acid sequence of QHREDGS (SEQ ID NO: 1). In some embodiments, the peptide consists of an amino acid sequence of QHREDGS (SEQ ID NO: 1). In some embodiments, the peptide comprises, consists essentially of, or consists of an amino acid sequence of REDG (SEQ ID NO: 3). In some embodiments, the peptide comprises, consists essentially of, or consists of an amino acid sequence of RLDG (SEQ ID NO: 4). In some embodiments, the peptide comprises, consists essentially of, or consists of an amino acid sequence of REDGS (SEQ ID NO: 5). In some embodiments, the peptide comprises, consists essentially of, or consists of an amino acid sequence of RLDGS (SEQ ID NO: 6). In some embodiments, the peptide comprises, consists essentially of, or consists of an amino acid sequence of HREDG (SEQ ID NO: 7). In some embodiments, the peptide comprises, consists essentially of, or consists of an amino acid sequence of HRLDG (SEQ ID NO: 8). In some embodiments, the peptide comprises, consists essentially of, or consists of an amino acid sequence of HREDGS (SEQ ID NO: 9). In some embodiments, the peptide comprises, consists essentially of, or consists of an amino acid sequence of HRLDGS (SEQ ID NO: 10). In some embodiments, the peptide comprises, consists essentially of, or consists of an amino acid sequence of QHREDG (SEQ ID NO: 11). In some embodiments, the peptide comprises, consists essentially of, or consists of an amino acid sequence of QHRLDG (SEQ ID NO: 12). In some embodiments, the peptide comprises, consists essentially of, or consists of an amino acid sequence of QHREDVS (SEQ ID NO: 13). In some embodiments, the peptide comprises, consists essentially of, or consists of an amino acid sequence of QHREDGS (SEQ ID NO: 14). In some embodiments, the peptide comprises, consists essentially of, or consists of an amino acid sequence of QHRLDGS (SEQ ID NO: 15). In some embodiments, the peptide comprises, consists essentially of, or consists of an amino acid sequence of KRLDGS (SEQ ID NO: 16). In some embodiments, the peptide comprises, consists essentially of, or consists of an amino acid sequence of QHREDGSL (SEQ ID NO: 17). In some embodiments, the peptide comprises, consists essentially of, or consists of an amino acid sequence of QHRLDGSL (SEQ ID NO: 18). In some embodiments, the peptide comprises, consists essentially of, or consists of an amino acid sequence of QHRLDGSLD (SEQ ID NO: 19). In some embodiments, the peptide comprises, consists essentially of, or consists of an amino acid sequence of QHREDGSLD (SEQ ID NO: 20).

In some embodiments, the composition or peptide of the invention comprise, consist essentially of, or consists of a non-naturally occurring peptide as described in U.S. Pat. No. 9,096,643, U.S. Publication Nos. US20180296631A1 and US20190328824A1, each of which are incorporated herein by reference in their entirety.

In some embodiments, the QHREDGS (SEQ ID NO: 1) peptide may be linear, cyclic, cross-linked or immobilized as long as the cell-protective activity of the peptide is retained. In addition, the peptide may form a broad U-shape to assume the native structural characteristics of this peptide as it exists in angiopoietin 1.

In still other embodiments, the QHREDGS (SEQ ID NO: 1) peptide may include modifications which do not substantially affect the U-shape of the core residues so as to retain the cell-protective activity of the peptide, e.g. integrin-binding activity. For example, the peptide may be modified to include one or more additional amino acid residues at either the C- or N-termini, or to include a terminal protecting group that may function to stabilize the peptide, protect the peptide from undesirable degradation or improve the activity thereof. Any chemical group which serves to protect peptide ends may be used. Useful N-terminal protecting groups include, for example, lower alkanoyl groups of the formula R—C(O)— wherein R is a linear or branched lower alkyl chain comprising from 1-5 carbon atoms. Examples of N-terminal protecting groups include the acetyl group and amino acid analogues lacking the amino function. Examples of suitable carboxyl terminal protecting groups include, for example, ester-forming alkyl groups, particularly lower alkyl groups such as methyl, ethyl and propyl, as well as amide-forming amino functions such as primary amine (—NH$_2$), as well as monoalkylamino and dialkylamino groups such as methylamino, ethylamino, dimethylamino, diethylamino, methylethylamino and the like. C-terminal protection can also be achieved using a decarboxylated amino acid analogue, such as agmatine. Of course, N- and C-protecting groups of even greater structural complexity may alternatively be incorporated, if desired.

In yet other embodiments, the QHREDGS (SEQ ID NO: 1) peptide may also be modified at one or more of its core amino acid residues, for example, to include a derivatized R-group. Suitable modifications include those which may stabilize the U-shape of the peptide, to optimize the activity thereof, or which function to protect the peptide from degradation.

III. Formulations

The present disclosure provides formulations, dosages and methods for administration of the compositions described herein (e.g. a peptide comprising QHREDGS (SEQ ID NO: 1)).

In some embodiments, the QHREDGS (SEQ ID NO: 1)-comprising peptide is soluble.

The disclosed compositions, pharmaceutical compositions, and formulations can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the "Physician's Desk Reference", 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

The composition or formulation of the present disclosure may further include one or more other components, including, but are not limited to: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, cetyl alcohol, cetearyl alcohol and vegetable gums such as xanthan gum; gelling agents, such as ester-terminated polyester amides, hydroxyethyl cellulose, hydroxypropyl cellulose, methylcellulose, hydroxypropyl methylcellulose, sodium hyaluronate, hyaluronic acid, sodium carbome or aloe gel; structuring agents; metal chelating agents such as EDTA or salts thereof; pigments; colorants; and pH adjusters. Representative pH adjusting buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers.

The composition or formulation of the present disclosure may further include one or more compatible cosmetically acceptable adjuvants commonly used and known in the art, including, but not limited to: colorants, pearls, chromalites, micas, pigments, dyes, fragrances, emollients, humectants (such as propanediol 1,3 glycerin), preservatives (such as benzyl alcohol, ethylhexylglycerin, benzoic acid, sorbic acid, gluconolactone, sodium benzoate or calcium gluconate), vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals.

The composition or formulation of the present disclosure may further include cosmetic ingredients including, but not limited to, a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of cosmetic ingredients and those used in the cosmetic or pharmaceutical fields, may can comprise from about 0.01% to about 20% of the total weight of the formulation.

The composition or formulation of the present disclosure may further include a sunscreen to protect the skin from damaging ultraviolet rays. In some embodiments, the sunscreen provides both UVA and UVB protection, by using either a single sunscreen or a combination of sunscreens. Exemplary sunscreens include, but are not limited to avobenzone, cinnamic acid derivatives (such as octylmethoxy cinnamate), octyl salicylate, oxybenzone, octocrylene, titanium dioxide, zinc oxide, or any mixtures thereof. The sunscreen may comprise from about 1 wt % to about 30 wt % of the total weight of the composition or formulation.

III-A. Topical Formulations

The compositions of the present disclosure may be provided in physiologically acceptable vehicles or carriers. The vehicle may be either hydrophobic or hydrophilic. Suitable, hydrophobic carriers include, for example, waxy non-ionic substances commonly used in cosmetics, such as esters and ethers of fatty alcohols and of fatty acids, with carbon chain length from C8 to C22, preferably from C8 to C15, or from C12 to C15.

Exemplary fatty hydrophobic carriers include, but are not limited to, isopropyl myristate, isopropyl palmitate, octyl palmitate, isopropyl lanolate, acetylated lanolin alcohol, the benzoate of C12-C15 alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate or isopropyl isostearate.

Exemplary suitable hydrophilic carriers may comprise, but are not limited to, water, lower alcohols (C1-6), glycols and alkoxylated glycols commonly used in cosmetics, including ethylene glycol, diethylene glycol, triethylene glycol, propylene glycol, dipropylene glycol, and the like.

The topically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils unless otherwise indicated. The emulsion may include an emulsifier, such as a nonionic, anionic or amphoteric surfactant, glyceryl stearate, Polysorbate 60, Cetearyl Olivate, Sorbitan Olivate, Sodium Stearyl Lactylate, Stearic Acid, PEG 100 Stearate or a gellant, typically in an amount from about 0.001% to about 5% by weight.

The topically acceptable vehicle may include but are not limited to water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 50% to about 99% by weight of the formulation.

In some embodiments, the peptides of the invention are formulated for delivery using targeted delivery systems. Exemplary targeted delivery systems include but are not limited to liposomes, microspheres (see, e.g., U.S. Pat. No. 5,770,222 to Unger et al), so that the components and/or active constituents can more readily reach and affect the subcutaneous layer of the area of application, e.g., face or neck, or the other area of the skin.

The peptides of the present disclosure may also be formulated in a formulation for topical administration. Examples of a topical formulation include, but are not limited to, a lotion, cream, serum, spray, aerosol, cake, ointment, essence, gel, paste, patch, pencil, towelette, mask, stick, foam, elixir, concentrate, and the like, particularly for topical administration. In some embodiments, the composition is formulated as a gel, a tincture, a cream, an ointment, a lotion, or an aerosol spray.

The topical formulation comprises a peptide from about 0.000001% by weight to about 20% by weight of the formulation. In some embodiments, the topical formulation comprises a peptide from about 0.00001% by weight to about 10% by weight of the formulation. In some embodiments, the topical formulation comprises a peptide from about 0.00001% by weight to about 5% by weight of the formulation. In some embodiments, the topical formulation comprises a peptide from about 0.00001% by weight to about 0.0001% by weight of the formulation. In some embodiments, the topical formulation comprises a peptide from about 0.00001% by weight to about 0.001% by weight of the formulation. In some embodiments, the topical formulation comprises a peptide from about 0.001% by weight or to about 1% by weight of the formulation.

In some embodiments, the topical formulation has a pH range from about 1 to about 13. In some embodiments, the topical formulation has a pH range of from about 2 to about 12. In some embodiments, the topical formulation has a pH range of from about 3.5 to about 7. In some embodiments, the topical formulation has a pH range of from about 7 to about 10.5. In some embodiments, the topical formulation has a pH range from about 3 to about 4, about 4 to about 5, about 5 to about 6, about 6 to about 7, about 7 to about 8, about 8 to about 9, about 9 to about 10, about 10 to about 11 or about 11 to about 12. Suitable pH adjusters, such as, but not limited to, sodium hydroxide, citric acid and triethanolamine may be added to bring the pH within the desired range.

III-B. Formulations Comprising Carriers

A formulation of the present disclosure may comprise a peptide described herein and at least one carrier. In some embodiments, the peptide may be conjugated to the carrier. In some embodiments, the peptide is dispersed in or immobilized on a carrier.

The formulation comprises a peptide described herein from about 0.000001% by weight to about 20% by weight of the formulation. In some embodiments, the formulation comprises a peptide from about 0.00001% by weight to about 10% by weight of the formulation. In some embodiments, the formulation comprises a peptide from about 0.00001% by weight to about 5% by weight of the formulation. In some embodiments, the formulation comprises a peptide from about 0.00001% by weight to about 0.0001% by weight of the formulation. In some embodiments, the formulation comprises a peptide from about 0.00001% by weight to about 0.001% by weight of the formulation. In some embodiments, the formulation comprises a peptide from about 0.001% by weight or to about 1% by weight of the formulation.

In some embodiments, the formulation comprises a carrier at about 10%, about 15%, about 20%, about 25%, about 30%, about 35%, about 40%, about 45%, about 50%, about 55%, about 60%, about 65%, about 70% or about 75% by weight of the formulation. In some embodiments, the formulation comprises a carrier at about 10% to about 40% by weight of the formulation. In some embodiments, the formulation comprises a carrier at about 20% to about 50% by weight of the formulation. In some embodiments, the formulation comprises a carrier at about 30% to about 60% by weight of the formulation. In some embodiments, the formulation comprises a carrier at about 40% to about 70% by weight of the formulation. In some embodiments, the formulation comprises a carrier at about 20% to about 50% by weight of the formulation.

The amount of peptide or combination of peptides as described herein in the formulation is not particularly limited and can be adjusted based by one of ordinary skill in the art based on the severity of the wound and other factors generally considered by the skilled artisan. In certain embodiments of the present disclosure, the concentration of peptide or combination of peptides present in the formulation is from about 10 µM to about 1000 µM. In still other embodiments, the peptide or combination of peptides are present in the formulation is from about 50 µM to about 800 µM; about 75 µM to about 750 µM; about 100 µM to about 600 µM; or about 150 µM to about 500 µM.

In some embodiments, the carrier is selected from hydrogel, glycerol, propylene glycol, chitosan, alginate, agarose, polyether, polyester, methylcellulose, hyaluronan, collagen, laminin, Matrigel®, fibronectin, vitronectin, poly-1-lysine, a proteoglycan, fibrin glue, a gel made by decellularization of an engineered or natural tissue, polyglycolic acid (PGA), polylactic acid (PLA), a combination of PGA and PLA such as PLGA, poly ε-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), a self-assembling peptide hydrogel, AcN-RARADADARARADADA-CNH (SEQ ID NO: 2), polyurethane, poly(isopropylacrylamide), poly(N-isopropylacrylamide), and a combination thereof.

In certain embodiments, the carrier is a hydrogel. In some embodiments, the hydrogel comprises at least one of chitosan, alginate, agarose, methylcellulose, hyaluronan, collagen, laminin, Matrigel, fibronectin, vitronectin, poly-1-lysine, proteoglycans, fibrin glue, gels made by decellularization of engineered and natural tissues, and a combination thereof. In some embodiments, the hydrogel comprises chitosan.

In some embodiments, the formulation comprises collagen at about 0.01%, about 0.02%, about 0.03%, about 0.04%, about 0.05%, about 0.06%, about 0.07%, about 0.08%, about 0.09%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9% or about 3.0% by weight of the formulation. In some embodiments, the formulation comprises collagen at about 0.02% to about 2% by weight of the formulation.

In some embodiments, the formulation comprises at least two carriers, at least three carriers, at least four carriers, or more.

In some embodiments, the formulation includes at least one water-based hydrogel. As non-limiting examples of such hydrogels, mention is made of hydrogels prepared from polyacrylic acids, povidones, celluloses, and aloe. In some embodiments, a carboxy-methylcellulose hydrogel is used.

In particular embodiments, the carrier is chosen from polymers, such as water-soluble polymers, polymers of neutral charge, or water-soluble polymers of neutral charge. The carrier may also be considered by the FDA to be generally regarded as safe (GRAS). As examples of carriers which may be used in accordance with the present disclosure, non-limiting mention is made of hydrogels, including cellulose containing hydrogels such as carboxy-methylcellulose (CMC).

In some embodiments, the formulation can also include at least one stabilizer. Such stabilizers may serve a variety of purposes. For example, stabilizers may be added to the formulation for the purpose of buffering the pH and/or the viscosity of carrier in the presence of various metal salts. The stabilizer may be natural or synthetic, and is optionally biodegradable and/or bioerodable. Non-limiting examples of pH stabilizers that are suitable for use in accordance with the present disclosure include buffering salts and organic chemical compounds such as triethanolamine (TEA), which is both a tertiary amine and a tri-alcohol. Citric acid is also suitable for use in the present disclosure as a pH stabilizer.

The peptide can be immobilized in or conjugated to a hydrogel by any means known in the art including, but not limited to, solvent casting. In particular embodiments, the hydrogel and the peptide are conjugated to using 1-ethyl-3-(3-dimethylaminopropyl) carbodiimide (EDC) chemistry. In such embodiments, the hydrogel and the peptide are dissolved in a solvent, such as saline, optionally containing a phosphate buffer. The dissolved materials are mixed with EDC and N-hydroxysulfosuccinimide (S—NHS) and reacted. After conjugation, the materials can be worked up using standard procedures and used to prepare a film or other composition for administration.

III-C. Pharmaceutical Formulations and Scaffolds

In certain embodiments, the invention provides a pharmaceutical formulation comprising at least one peptide described herein.

In some embodiments, the pharmaceutical formulation further comprises at least one excipient, such as a water-soluble polymer, a surfactant, and/or another enhancer such as a pharmaceutically acceptable excipient. Non-limiting examples of pharmaceutically acceptable excipients are described in Remington's Pharmaceutical Sciences by E. W. Martin, and include cellulose, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In some embodiments, the pharmaceutical formulation also contains pH buffering reagents, and wetting or emulsifying agents.

The pharmaceutical formulation can be in the any form suitable for administration to a patient, such as in the form of an aqueous dispersion or suspension. The pharmaceutical formulation may also contain various additional ingredients, such as suspending, stabilizing and/or dispersing agents.

In some embodiments, the pharmaceutical formulations are in the form of a controlled-release formulation.

In particular embodiments, the pharmaceutical formulation of the invention is adhered to a backing or dressing for application as a patch or bandage. In such embodiments, the pharmaceutical patch according to the invention comprises a backing layer and a pharmaceutical layer. The construction and use of transdermal patches for the delivery of pharmaceutical agents is well known in the art. Such patches may be constructed for continuous, pulsatile, or on demand delivery of pharmaceutical agents.

The term "pharmaceutical layer" as used herein refers to any layer comprising a peptide and a hydrogel as defined herein.

The term "backing layer" as used herein refers to any layer that represents the surface layer after the application of the pharmaceutical patch. This definition includes permanent backing layer commonly used for pharmaceutical patches as well as thin non-removable films that are typically used in thin flexible patches.

In some embodiments, the backing layer comprises one or more polymers selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride, polyesters and polyolefins, such as polyethylene; polyolefins, in particular polyethylene, polyesters, ethylene vinylacetate copolymers and polyurethanes are particularly preferred. Other materials which can be used to form the backing include, but are not limited to, modified cellulosics such as cotton, rayon, ramie and the like; modified polyolefins such as low-density polyethylene and polypropylene, modified polyesters and modified poly(acrylonitriles). Examples of particular materials of these types include oxidized cellulosics; phosphorylated cellulosics; carboxymethylated cellulosics; succinylated cellulosics; grafts of polyolefins such as polypropylene with polyacrylics such as polyacrylic acid, hydrolyzed poly(acrylamides), polyacrylates, and poly(acrylonitriles); grafts of cellulosics with polyacrylics such as polyacrylic acid, hydrolyzed poly(acrylamides), polyacrylates and poly(acrylonitriles); sulfonated polyolefins; partially hydrolyzed poly(acrylonitriles) and partially hydrolyzed polyesters.

The backing layer may be a non-woven fabric or a laminate. In certain embodiments, the backing layer comprises a polymer film, such as a polyester film, and a heat seal layer.

The thickness of the backing layer is not particularly limited. In some embodiments, the backing layer has a thickness within the range of from 0.1 µm to 5000 µm; from 0.5 µm to 1000 µm; from 1 µm to 750 µm; from 5 µm to 500 µm; or from 10 µm to 250 µm.

The pharmaceutical patch according to the invention optionally comprises a removable protective layer (release liner).

In certain embodiments, the removable protective layer comprises a polymer film and a silicone coating or fluoropolymer coating. In particular embodiments, the polymer film is a polyolefin, in particular polyethylene or polypropylene film or polyester, in particular polyethylene terephthalate film.

In an additional aspect, the description provides a tissue scaffold comprising a peptide and a carrier as described herein, wherein the peptide is immobilized to the carrier. In certain embodiments, the peptide is conjugated to a hydrogel within the tissue scaffold.

In any of the aspects or embodiments described herein, the tissue scaffold is in the form of a sheet, a graft, a bead, a wafer, a chip, a disc, a tube, a cylinder or a cone.

In any of the aspects or embodiments, the tissue scaffold further comprises an acidifying agent, an alkalinizing agent, an adsorbent, an aerosol propellant, an air displacement agent, an antifungal preservative, an antimicrobial agent, an antimicrobial preservative, an antioxidant, a binding material, a buffering agent, a carrying agent, a chelating agent, a colorant, a clarifying agent, an emulsifying agent, an encapsulating agent, a flavor ant, a humectant, a levigating agent, an oil, an ointment base, a penetration enhancer, a plasticizer, a stiffening agent, a surfactant, a suspending agent, a thickening agent, a tonicity agent, a viscosity increasing agent, a wetting agent, or a combination thereof.

In any of the aspects or embodiments, the tissue scaffold further comprises an additional active agent.

In any of the aspects or embodiments described herein, the tissue scaffold is configured for use in vitro or for use in in vivo tissue growth, grafting, repair or combinations thereof.

In some embodiments, the tissue scaffold of the invention further comprises at least one stabilizer.

In any of the aspects or embodiments described herein, the described compositions and formulations can be used alone or in combination with another therapeutic agent to treat such conditions. It should be understood that the compositions and formulations of the invention can be used alone or in combination with an additional active agent, e.g., a therapeutic agent, said additional agent being selected by the skilled artisan for its intended purpose. For example, the additional agent can be a therapeutic agent art-recognized as being useful to treat the disease or condition being treated by the compositions and formulations of the present disclosure. The additional agent also can be an agent that imparts a beneficial attribute to the therapeutic composition e.g., an agent that affects the viscosity of the composition of formulation.

IV. Methods of Use

The present disclosure demonstrates that the peptide comprising QHREDGS (SEQ ID NO: 1) is able to induce a novel macrophage polarization state. This novel macrophage polarization state can be characterized by a shift in the CD86/CD206 expression, as well as increases in both pro-inflammatory, and anti-inflammatory cytokines. Such an effect on macrophage polarization may play a role in the success of the peptide for wound healing applications.

Accordingly, one aspect of the present disclosure relates to a method of inducing a polarization state of a macrophage, the method comprising contacting the macrophage with a formulation of the present disclosure. In some embodiments, the formulation comprises a peptide that comprises the amino acid sequence QHREDGS (SEQ ID NO: 1).

In some embodiments, the induced polarization state can be characterized by an increase in release of a pro-inflammatory cytokine and an increase in anti-inflammatory cytokine production by the macrophage relative to a macrophage that has not been contacted with the formulation.

In some embodiments, the pro-inflammatory cytokine can be selected from IFN-γ, IL-1β, GM-CSF, IL-6, IL-12, MCP-1, TNF-α, and a combination thereof.

In some embodiments, the anti-inflammatory cytokine can be selected from IL-4, IL-10, TGF-β, and a combination thereof.

In some embodiments, the induced polarization state can be characterized by an increase in the ratio of TGF-β3/TGF-β1 released by the macrophage relative to a macrophage that has not been contacted with the formulation.

In some embodiments, the induced polarization state can be characterized by an increase in expression level of CD86 and a decrease in expression level of CD206 on the macrophage relative to a macrophage that has not been contacted with the formulation.

In some embodiments, the induced polarization state can be characterized by at least one of or a combination of the following: (a) an increase in release of a pro-inflammatory cytokine and an increase in anti-inflammatory cytokine production by the macrophage relative to a macrophage that has not been contacted with the formulation; (b) an increase in the ratio of TGF-β3/TGF-β1 released by the macrophage relative to a macrophage that has not been contacted with the formulation; and (c) an increase in expression level of CD86 and a decrease in expression level of CD206 on the macrophage relative to a macrophage that has not been contacted with the formulation.

The contacting step can be performed in vitro or in vivo.

The novel macrophage polarization state described herein can be used as an indicator of the effectiveness of a composition (e.g., a peptide) or formulation in mediating wound healing. For example, if a composition or formulation can induce the novel polarization state in a macrophage, then the composition or formulation can be effective in mediating wound healing. As such, the present disclosure relates to the use of such composition or formulation for mediating wound healing.

One related aspect of the present disclosure relates to a method of modulating a polarization state of a macrophage from a subject, the method comprising: (a) contacting the macrophage with a composition or a formulation; (b) measuring expression levels of a pro-inflammatory marker and an anti-inflammatory biomarker and/or release of a pro-inflammatory cytokine and an anti-inflammatory cytokine by the macrophage in response to the contacting step; and (c) determining the polarization state after the contacting step based on a result obtained from the measuring step.

In some embodiments, the formulation comprises an angiopoietin-1 mimetic peptide.

In some embodiments, the measuring step comprises measuring a change in the expression levels of the pro-inflammatory marker and the anti-inflammatory marker by the macrophage relative to a macrophage that has not been contacted with the composition or formulation. Any method known in the art for measuring the expression level of a protein can be used. In some embodiments, the pro-inflammatory marker is CD86. In some embodiments, the anti-inflammatory marker is CD206.

In some embodiments, the measuring step comprises measuring a change in release of the pro-inflammatory cytokine and an anti-inflammatory cytokine by the macrophage relative to a macrophage that has not been contacted with the composition or formulation. In some embodiments, the pro-inflammatory cytokine is selected from IFN-γ, IL-1β, GM-CSF, IL-6, IL-12, MCP-1, TNF-α, and a combination thereof. In some embodiments, the anti-inflammatory cytokine is selected from IL-4, IL-10, TGF-β, and a combination thereof.

If the polarization state after the contacting step is characterized by one or more of the following changes by the macrophage relative to a macrophage that has not been contacted with the composition or formulation: (a) an increase in release of the pro-inflammatory cytokine and the anti-inflammatory cytokine by the macrophage; (b) an increase in the ratio of TGF-β3/TGF-β1 released by the macrophage; and/or (c) an increase in expression level of CD86 and a decrease in expression level of CD206 on the macrophage, then the method further comprises administering the composition or formulation to a subject in need thereof to mediate wound healing.

Yet another aspect of the present disclosure relates to a method of treating a wound in a subject in need thereof, the method comprising administering the composition or formulation that can induce the novel macrophage polarization state as described herein to the wound of the subject. In some embodiments, the treatment can result in the healed wound substantially free of scars. In some embodiments, the treatment can result in scarless wound healing.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

EXAMPLES

The following are examples of methods and compositions of the invention. It is understood that various other embodiments may be practiced, given the general description provided above.

Example 1

A. Peptide Modified Chitosan Conjugation

Either the Q-Peptide (QHREDGS (SEQ ID NO: 1) with biotin-Ahx N-terminal modification, Genscript) or the scrambled Q-Peptide (DGQESHR (SEQ ID NO: 22), Biomatik) was conjugated to chitosan as previously described using 1-ethyl-3-(3-dimethylaminopropyl) carbodiimide (EDC) chemistry. Briefly, chitosan (Heppe Medical Chitosan) was dissolved in 0.9% normal saline at 20 mg/mL and the peptide was dissolved in phosphate buffered saline (PBS, Gibco) at 10 mg/mL. EDC (Thermo Scientific) and N-hydroxysulfosuccinimide (S—NHS, Thermo Scientific) were dissolved in PBS and mixed with the chitosan and the peptide to achieve a final concentration of 5 mg/mL and 3 mg/mL respectively. The solution was mixed on a vortex for 3 hours, and diluted 4× in PBS before being dialyzed against distilled, deionized water for 24 hours (Spectra/POR MWCO 3500, Spectrum Labs). The solution was sterile filtered and lyophilized for 48 hours. The resulting chitosan conjugated peptide was stored at −20° C. until further use. After dialysis, the conjugation efficiency was validated using the Pierce™ Biotin Quantitation Kit (Thermo Scientific) as per the manufacturer's instructions. The absorbance was measured at 500 nm. Concentration of biotin (and therefore peptide concentration) was calculated. As a positive control, 0.1 mg/mL QHREDGS (SEQ ID NO: 1) peptide was used to calculate moles of biotin per mole of protein to verify assay performance (1:1 ratio biotin to peptide).

B. Collagen-Chitosan Hydrogel Formation

The crosslinked hydrogel was prepared as previously described. Type I collagen (Corning) and chitosan (with or without conjugated peptide) were mixed for a final concentration of 2.5 mg/mL. PBS (10×) was added at 10% of the final volume, and the solution was neutralized.

C. Degradation

To assess the in vitro enzymatic degradation, 1.7 mL Eppendorf tubes were weighed, and 500 μ, of hydrogel was added to each tube and allowed to gel as previously described. Collagenase solution (1 ml, 1 U/mL) (Worthington Biochemical Corporation), lysozyme (100 U/mL) (Sigma), or PBS was added to the tube and placed on a shaker (100 rpm) at 37° C. Enzymatic solution or PBS was changed every 48 hours, and the tubes and gels were collected and frozen at −80° C. on days 0, 1, 3, 5, 7, 10, and 14 (n=3/time point). All samples were lyophilized together and weighed. Degradation was calculated by comparing the final weight to that of the group collected immediately after gelation on day 0.

D. Solvent Casting of Chitosan-Collagen Films

For in vitro experiments, chitosan-collagen films were solvent cast in cell culture well plates. Chitosan (with or without conjugated Q-Peptide or scrambled Q-Peptide) was dissolved in 0.5N acetic acid at 2 mg/mL and mixed with 2 mg/mL type 1 collagen. Non-adherent 6-well plates were coated with 750 µL per well. The coating solution was fully evaporated in a biosafety hood, leaving behind a chitosan-collagen film. Prior to use, the films were washed 3× with PBS.

E. Bone Marrow Derived Macrophage Isolation

Figure 6A:
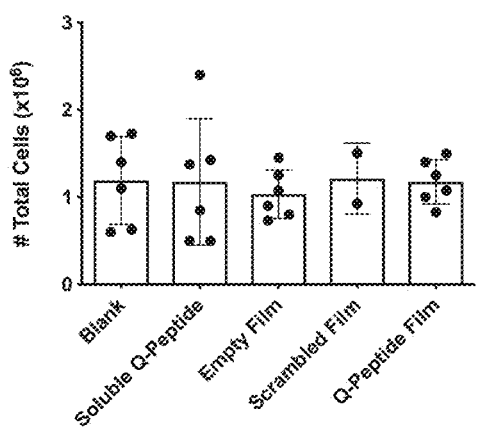
FIGS. 6A-6B show macrophage characteristics when cultured on the Q-Peptide hydrogel film.
Figure 6B:
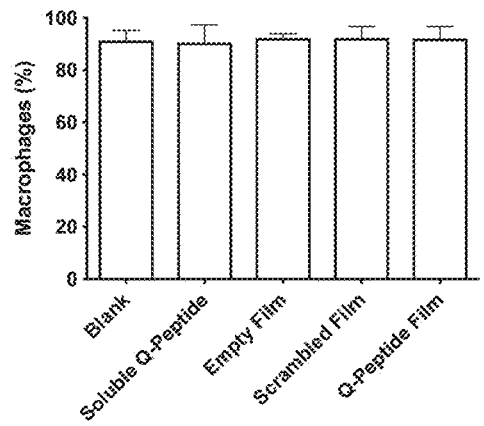

Murine bone marrow derived macrophages (BMDM) were isolated from 8-12 week-old C57BL/6 mice (Charles River) according to a protocol approved by the University of Toronto Animal Care Committee. The mice were euthanized, and the femur and tibias were removed and placed in complete RPMI 1640+L-glutamine media (Gibco, 10% heat inactivated Fetal Bovine Serum, FBS, 1% Pen/Strep). The bones were separated and sterilized in 70% ethanol for 10 minutes. The heads of the bones were cut off, and the marrow was flushed out with a 23 G needle containing fresh complete RPMI 1640 media. The remaining cell culture media and bone marrow was homogenized by gentle pipetting. The cells were spun down and resuspended in ACK Lysing Buffer (Gibco) for 1 min to lyse remaining red blood cells. The lysing buffer was diluted with PBS, and the cell suspension was re-spun, and counted. Cells were seeded at 3 million cells/well in non-adherent 6-well culture plates containing 2 mL of complete RPMI 1640 media with 20 ng/mL of Macrophage Colony Stimulating Factor (M-CSF, Miltenyi Biotec). Half (50%) of the media was changed on day 3, and 5. On day 7, adherent cells were used as macrophages for experiments. Macrophage purity, as identified by F4/80+, CD11b+ positive staining, under all culture stimulations is >90%, consistent with previous studies (FIG. 6B).

F. BMDM Polarization

Adherent macrophages were detached by incubating with 0.25% trypsin-EDTA for 10 minutes. Cells were polarized in response to the following treatment conditions: blank-included cultivation on tissue culture plastics; soluble Q-Peptide (650 µM) applied to macrophages cultivated on tissue culture plastics; and macrophages cultivated on the following hydrogel films: no peptide collagen-chitosan (empty) film, scrambled Q-Peptide film, and Q-Peptide film. BMDMs were polarized with lipopolysaccharide (LPS; 100 ng/mL) for pro-inflammatory, M(LPS), and IL-4 (long/mL) for anti-inflammatory, M(IL-4) positive polarization controls. Cells were seeded directly onto a non-adherent 6-well plate for the blank and soluble Q-Peptide conditions, and onto solvent cast films for the empty film, scrambled Q-Peptide film, and Q-Peptide film at a concentration of 100,000 cells/cm$^2$. After 24 hours of culture, cell culture media was collected for ELISA analysis by Eve Technologies (Calgary, AB), and the concentrations of INF-$\gamma$, IL-1$\beta$, IL-2, IL-4, IL-6, IL-10, IL-12 p'70, GM-CSF, MCP-1, TNF-$\alpha$, TGF-$\beta$31, TGF-$\beta$2, and TGF-$\beta$3 were measured.

G. FACS Analysis

Figure 7:
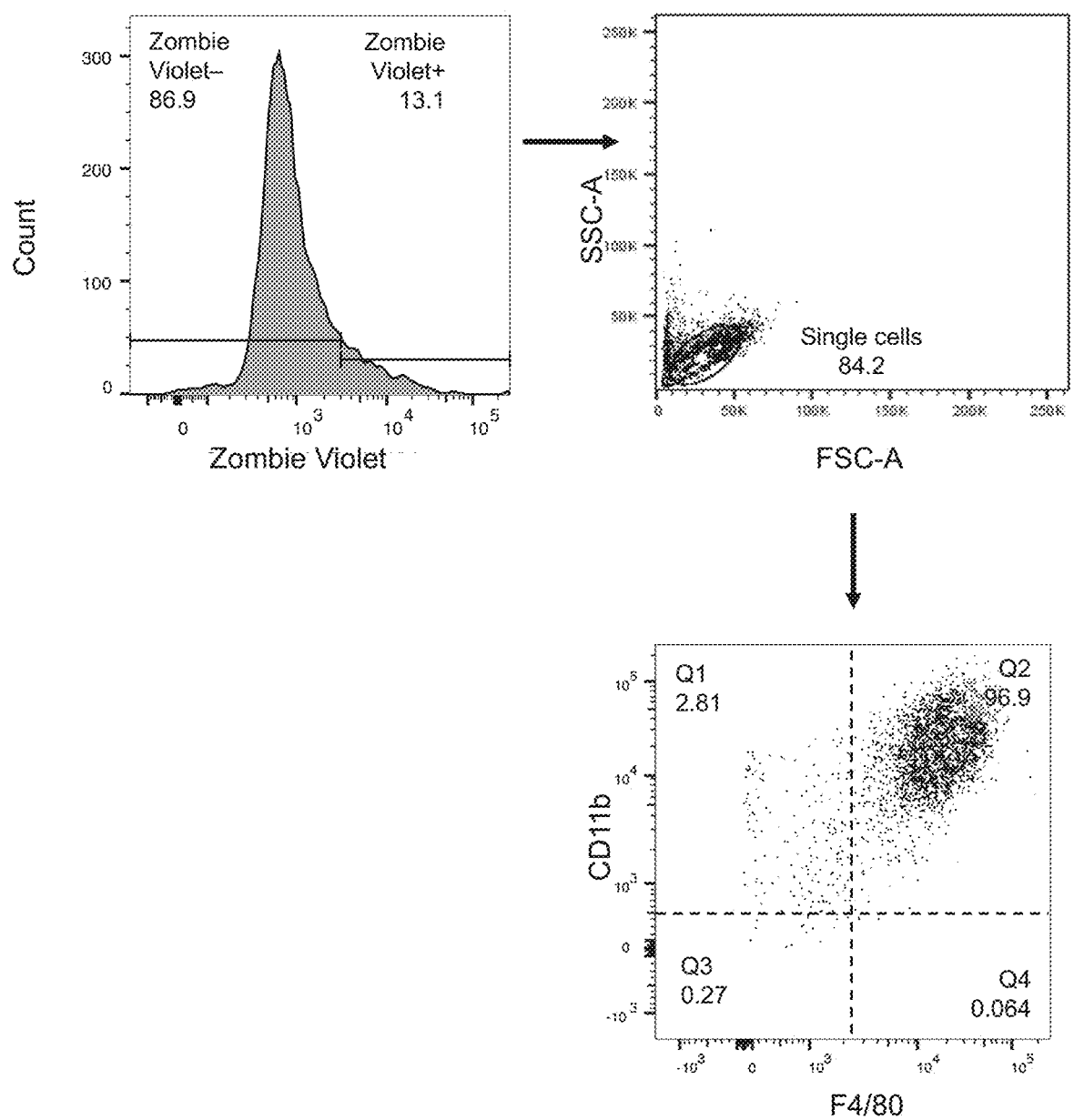
FIG. 7 shows gating strategy for single cell assessment of macrophage polarization. Macrophages were first gated for live cells as defined by negative staining of Zombie Violet. Cells were then gated for single cell population, followed by F480+ and CD11b+.
Figure 8A:
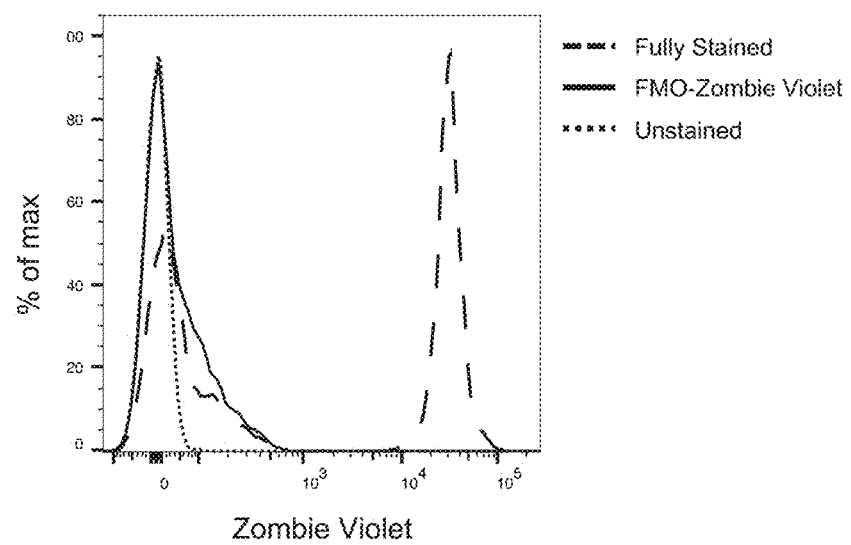
FIGS. 8A-8C shows florescence minus one staining controls.
Figure 8B:
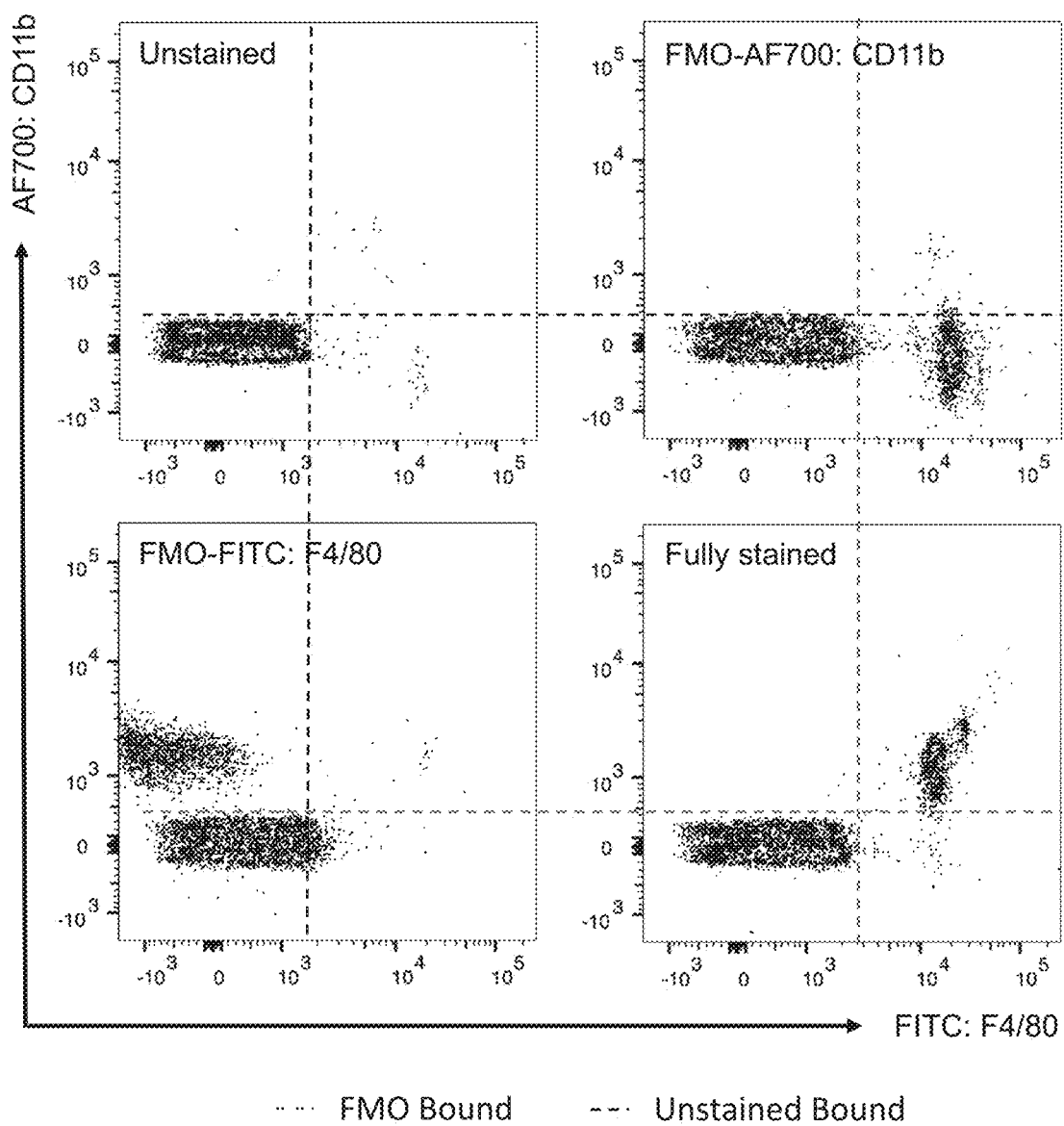
Figure 8C:
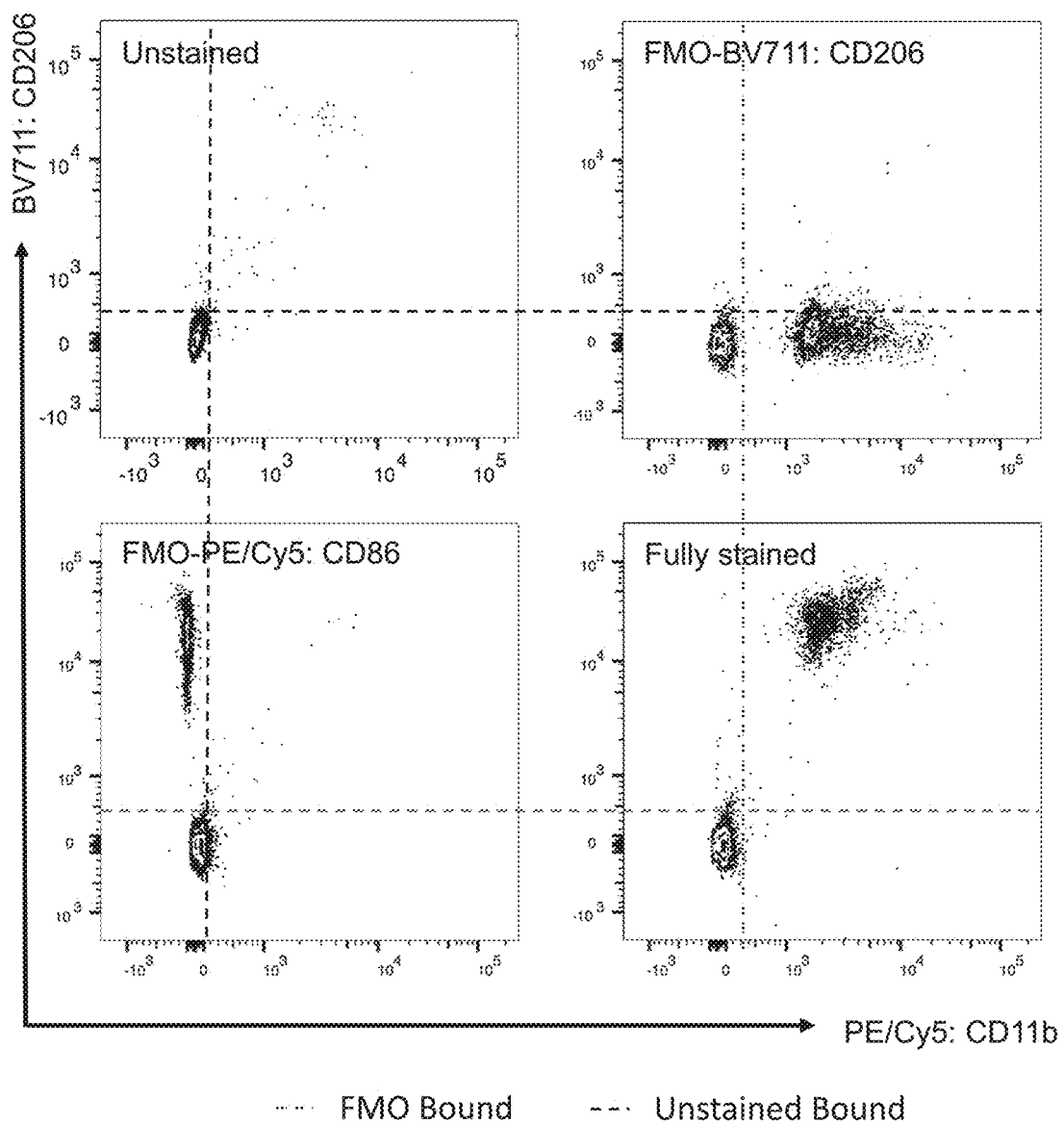

Following macrophage polarization, the supernatant was collected, and cells were detached by incubating with 0.25% trypsin-EDTA for 10 minutes. Cells cultured on the collagen-chitosan films or peptide films were subjected to light scraping to disrupt the film and were passed through a 70 µm pore cell strainer to filter any remaining hydrogel film. The cells were first stained with Zombie Violet Fixable Viability Kit (BioLegend, 423114). Non-specific receptors, CD16/CD32 were blocked with TruStain FcX (BioLegend, 101320). Finally, BMDMs were surface stained for F4/80 (BioLegend, 123107), CD11b (Biolegend, 101261), CD86 (Biolegend, 105015), and CD206 (Biolegend, 141727). Macrophages were identified as F4/80+CD11b+, and further characterized as pro-inflammatory or anti-inflammatory based on CD86, and CD206 staining respectively. Positive staining and compensation for each was performed using (Thermo Fisher, 01-2222-41), and ArC Amine Reactive Compensation Bead Kit (Thermo Fisher, A10628). Flow cytometry was performed using the BD LSRII-SC VBR (Flow and Mass Cytometry Facility at TMDT and PGCRL). Macrophages were gated by positive staining of CD11b and F4/80. Gating strategy can be found in FIG. 7 and FMO controls in FIGS. 8A-8C.

H. Statistical Analysis

All results are presented as mean±SD. Statistical analysis was performed using GraphPad Prism 6. Normality and equality of variances was tested using Shapiro-Wilk test and Brown-Forsythe test respectively. Significance was calculated using either a one-way ANOVA, Brown-Forsythe and Welch's ANOVA test, or a Kruskal-Wallis test. To identify significant differences between experimental groups, either a Tukey's multiple comparisons test, Dunnett's T3 multiple comparisons test, or Dunn's multiple comparisons test was employed. A value of P<0.05 was considered statistically significant.

I. Development and Characterization of the Q-Peptide Hydrogel Patch

Figure 1B:
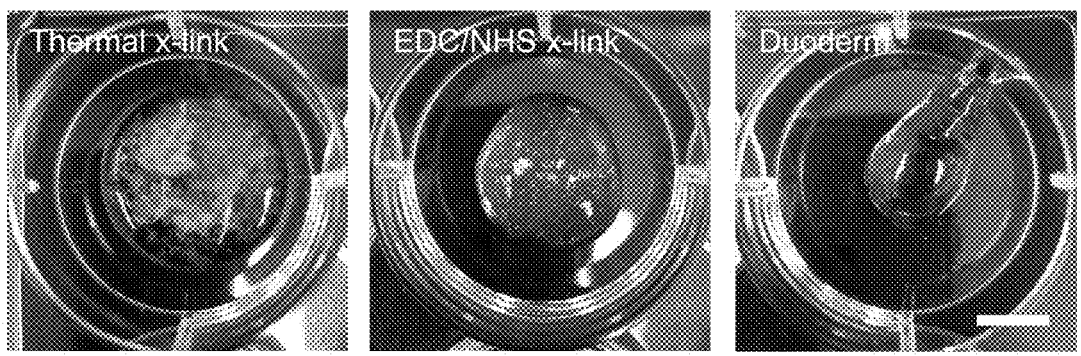
Figure 1C:
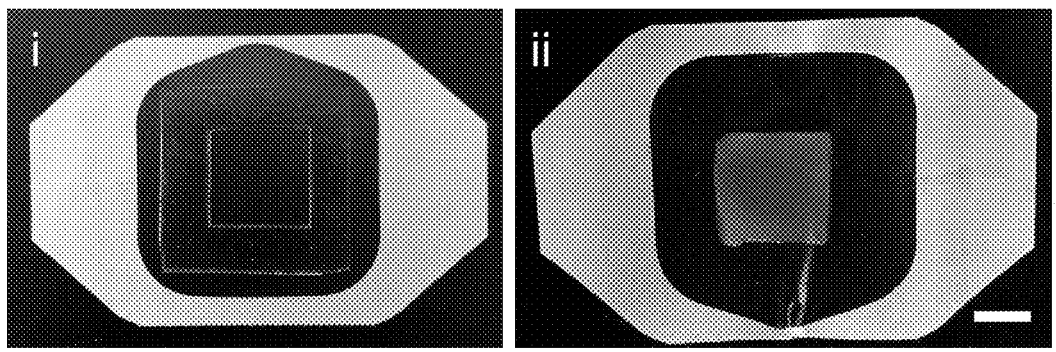

The Q-peptide hydrogel was optimized to be delivered as either a homogenous viscous gel, or a hydrogel patch (FIG. 1A) for improved clinical delivery. When extruded from a syringe, the thermally gelled Q-Peptide hydrogel is a heterogenous solution with short chains of crosslinked collagen-chitosan hydrogel suspended in water (FIG. 1B, i). As a result, EDC and NHS chemistry was used to chemically crosslink the hydrogel to increase the stability and injectability. Similarities in the physical appearance between the EDC/NHS crosslinked hydrogel, and Duoderm, a Food and Drug Administration (FDA) approved wound product, can be seen in the gross morphology (FIG. 1B, ii-iii). Further, a hydrogel patch was proposed as an additional delivery mechanism for the material. The patch was created by casting the pre-gelled hydrogel into a polydimethylsiloxane (PDMS) mold. Upon gelation, the PDMS mold was removed, leaving a thin hydrogel film. FIG. 1C shows a 2 cm×2 cm square patch, with a gel thickness of 1 mm.

Figure 1D:
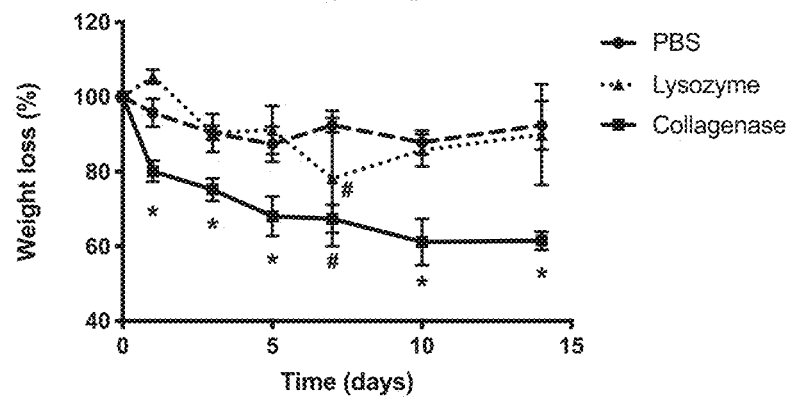

The enzymatic degradation of the Q-Peptide hydrogel was evaluated to assess the rate at which the hydrogel degrades in enzymatic conditions similar to those in vivo. After 14 days, the material exhibited a weight loss of 92±5%, 90±11%, and 61±2% in PBS, lysozyme, and collagenase respectively (FIG. 1D).

J. Bone Marrow Derived Macrophage Culture on Hydrogel Films

To examine the polarization effect of the Q-Peptide on macrophages, BMDMs were cultured in the presence of the soluble Q-Peptide (650 μM), no peptide collagen-chitosan film (empty film), scrambled peptide hydrogel film, and the Q-peptide hydrogel film (FIG. 2A). After 24 hours, cell attachment on the peptide hydrogel films was not significantly different from each other and the blank culture conditions (FIG. 2B), although they were significantly higher than the soluble Q-Peptide and the empty film. The decrease in cell attachment in the soluble Q-Peptide and empty film condition did not affect the final cell count, which included cells in solution and those that had attached (FIG. 6A). Further, the viability of the BMDMs, as measured by the fixable Zombie Violet stain, was not affected by the culture conditions (FIG. 2C). Viability for all polarization treatments was >75%.

K. Q-Peptide Films Induces Macrophage Marker Expression

Figure 3A:
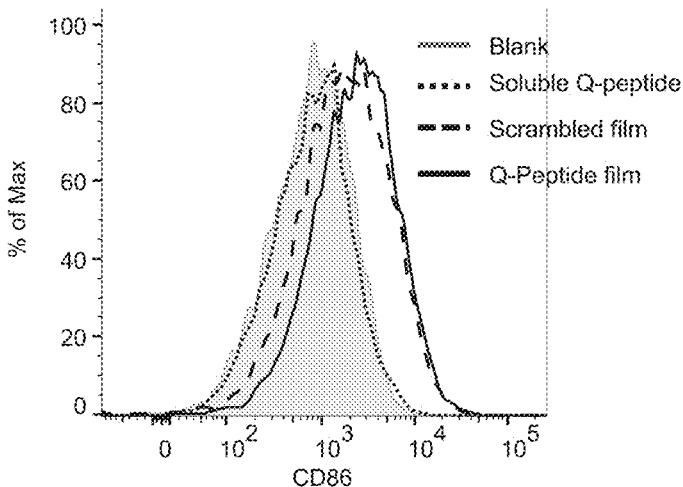
FIGS. 3A-3D shows that the covalently immobilized Q-Peptide shifts the expression of macrophage markers. Representative histogram for the expression of (FIG. 3A) CD86, and (FIG. 3B) CD206 for BMDMs cultured in blank (grey), soluble Q-peptide (black dots), scrambled peptide film (black dash), and Q-Peptide film (solid black).
Figure 3B:
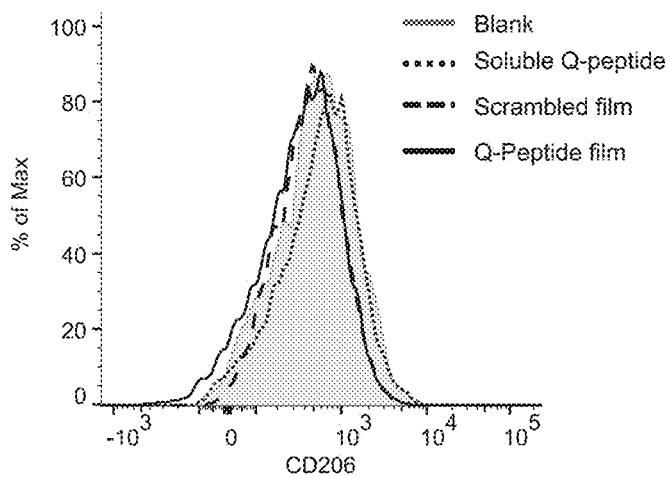
Figure 3C:
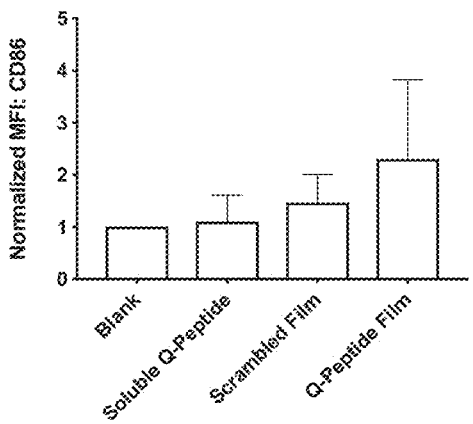
Figure 3D:
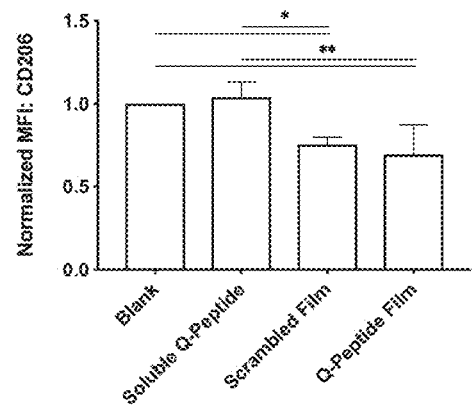

Flow cytometry was performed to assess the macrophage polarization towards a proinflammatory phenotype or an anti-inflammatory phenotype. Polarization phenotype was evaluated by the expression of known pro- and anti-inflammatory markers, CD86 and CD206 respectively. FIGS. 3A and 3B are representative histograms of CD86 and CD206 expression respectively. The distribution of CD86 and CD206 expression for BMDMs cultured in the presence of the soluble Q-Peptide was similar to that of the blank, untreated cells. There is an increasing trend in the median fluorescence intensity (MFI) of CD86 when BMDMs were cultured on the Q-Peptide film (FIG. 3C), and a significant decrease in the normalized MFI of CD206 when BMDMs were cultured on the Q-Peptide film, and the scrambled peptide film in comparison to the blank and soluble controls (FIG. 3D).

L. Q-Peptide Films Stimulate Cytokine Release

Figure 4A:
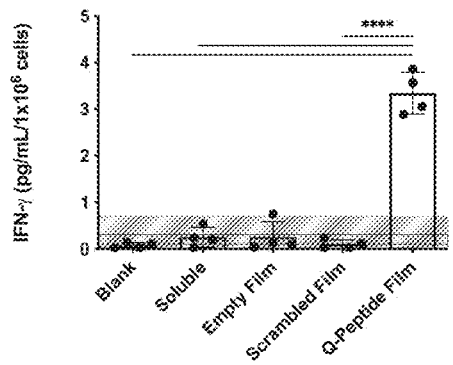
FIGS. 4A-4J show the Q-Peptide film modulates macrophage cytokine inflammatory response. ELISA analysis reveals an upregulation of (FIG. 4A) IFN-γ (FIG. 4B) IL-1β (FIG. 4C) GM-CSF (FIG. 4D) IL-2 (FIG. 4E) IL-4 (FIG. 4F) IL-6 (FIG. 4G) IL-10 (FIG. 4H) IL-12 (FIG. 4I) MCP-1 (FIG. 4J) TNF-α when BMDMs are cultured with blank, soluble Q-Peptide, empty film, scrambled film, and Q-Peptide film (n=4). Angled line shading: concentration with LPS stimulation, Dot shading: concentration with IL-4 stimulation. Data is normalized to total cell number (pg/mL/1×10$^6$ cells). Data are presented as mean±SD.  p<0.01, * p<0.001, **** p<0.0001.
Figure 4B:
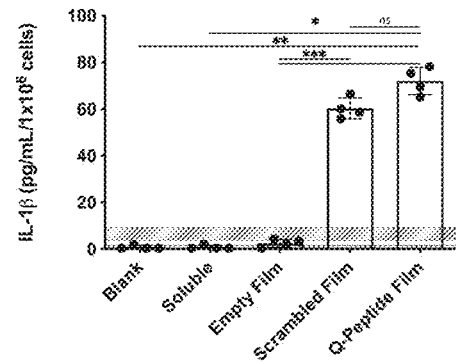
Figure 4C:
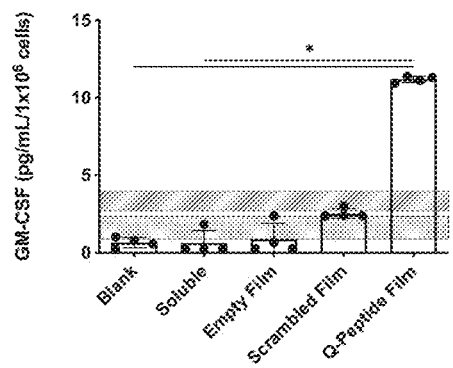
Figure 4D:
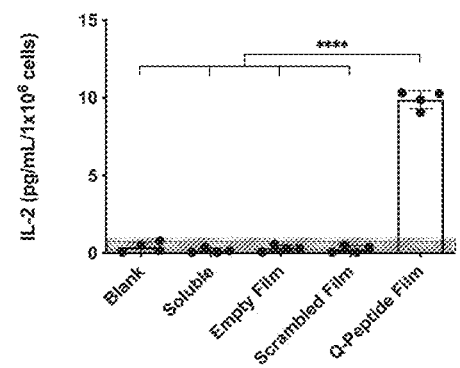
Figure 4E:
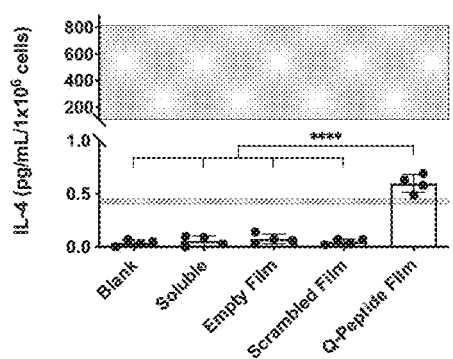
Figure 4F:
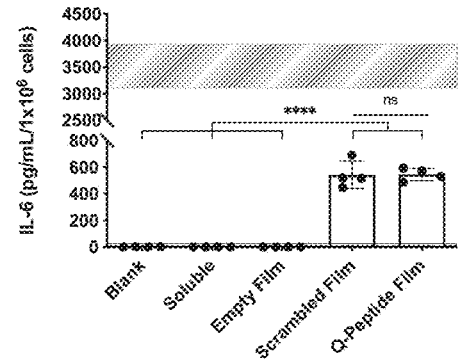
Figure 4G:
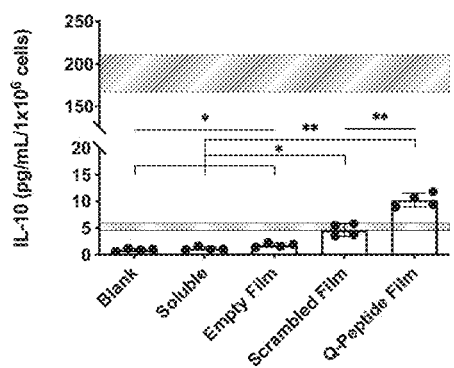
Figure 4H:
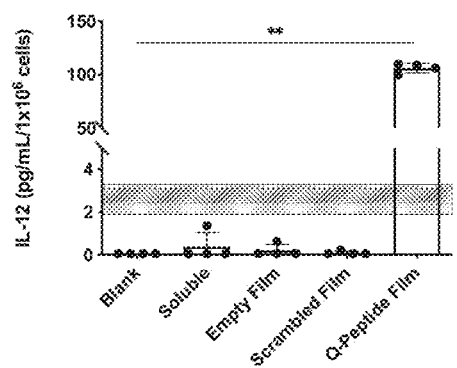
Figure 4I:
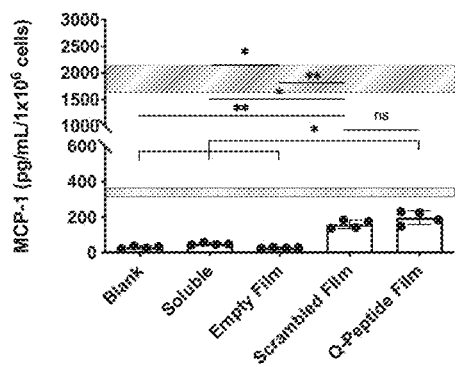
Figure 4J:
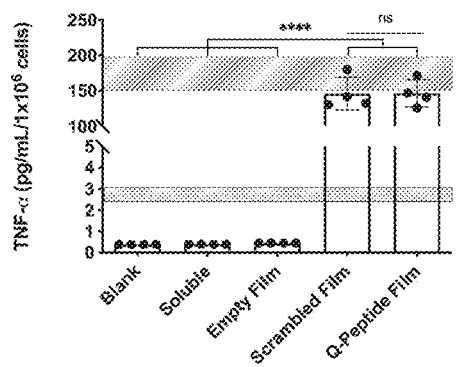

After 24 hours of culture, ELISA was performed on the culture media to determine the concentration of cytokines produced by the macrophages (FIG. 4A-4J) Cytokine release from BMDMs stimulated with LPS are indicated by the blue shaded areas, and the red areas indicate those polarized with IL-4. A significant increase in the concentration of IFN-γ, IL-2, IL-4, and IL-10 (FIGS. 4A, 4D, 4E, 4G) was observed when BMDMs were cultured on the Q-Peptide films relative to the other culture conditions. Further, the Q-Peptide films caused a significant increase in the concentration of IL-1β compared to the blank, soluble Q-Peptide, and the empty films (FIG. 4B). There was an increasing trend in the release of GM-CSF and IL-12 when BMDMs were cultured on the Q-Peptide film (FIGS. 4C, 4H), Interestingly, BMDMs cultured on both the scrambled film and the Q-Peptide film resulted in a significant increase in the concentrations of IL-6, MCP-1, and TNF-α (FIGS. 4F, 4I, 4J), compared to the blank, soluble Q-Peptide, and empty film, although there was no significant difference in the concentrations between the two peptide films, suggesting a non-specific response to the presence of amino acids.

Figure 5A:
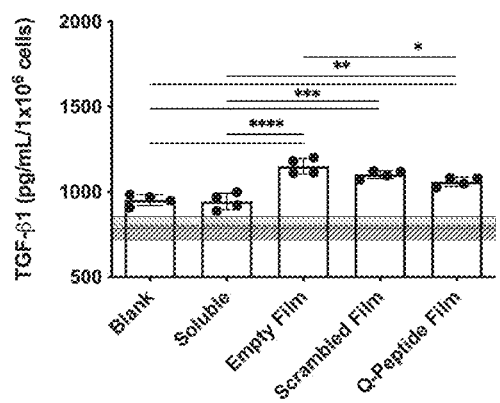
FIGS. 5A-5D shows that the Q-Peptide films modulates TGF-β release from macrophages. ELISA analysis demonstrates maintenance of (FIG. 5A) TGF-β1 release (FIG. 5B) TGF-β2 release and an upregulation of (FIG. 5C) TGF-β3 release and an increase in the (FIG. 5D) TGF-β3/TGF-β1 ratio. (n=4). Angled line shading: concentration with LPS stimulation, Dot shading: concentration with IL-4 stimulation. Data is normalized to total cell number (pg/mL/1×10$^6$ cells). Data are presented as mean±SD.  p<0.01, * p<0.001, **** p<0.0001.
Figure 5B:
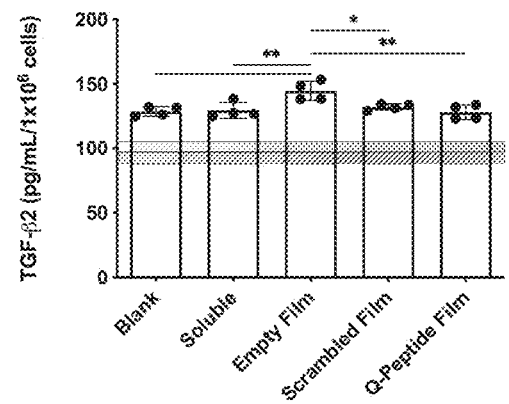
Figure 5C:
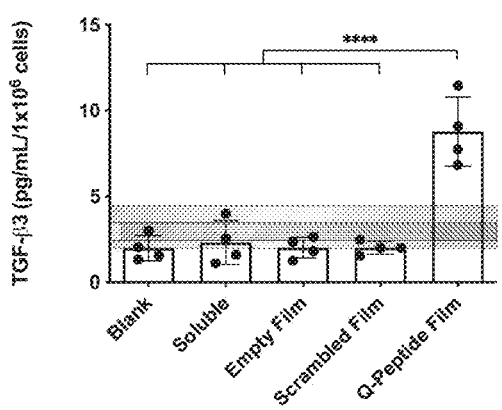
Figure 5D:
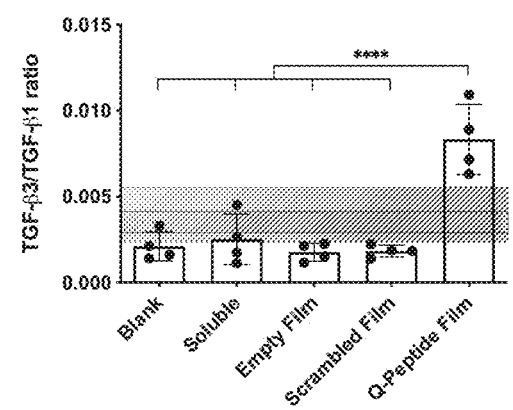

In addition, the concentration of three different isoforms of TGF-β were measured. The empty film stimulated a significant increase of TGF-β1 and TGF-β2 (FIGS. 5A, 5B), while the Q-Peptide film stimulated a significant increase in the release of TGF-β3 (FIG. 5C). Further, there was a significant difference in the ratio of TGF-β3/TGF-β1 on the Q-Peptide film compared to all other controls (FIG. 5D).

M. Discussion

One obstacle to overcome in the development of a hydrogel wound dressing is the delivery of the material in an easy to apply manner. In our previous work, the Q-Peptide hydrogel was applied as a pre-gelled solution in a murine myocardial infarction model and a diabetic wound healing model. In both cases, the gel was pre-warmed at 37° C. for 10 minutes to initiate gelling, at which point it was injected into the animal where gelling continued. This method is impractical in a clinical setting as it is cumbersome to prepare the pre-gelled material before each use and is greatly dependent on the technical skill of the healthcare practitioner. Further, as the hydrogel requires approximately 30 minutes to fully crosslink, it is difficult to ensure a localized delivery as the hydrogel is susceptible to flowing to other regions other than the intended delivery site. Hydrogels currently approved by the FDA are supplied as a crosslinked, amorphous gel, or a sheet. As a result, we sought to re-design the delivery and physical presentation of the hydrogel to more closely match a product that healthcare practitioners are already familiar with.

Carbodiimide was selected as a crosslinking chemistry because it does not result in the incorporation of the crosslinker into the hydrogel, as is the case with other crosslinkers such as glutaraldehydes, or genipin. In addition, glutaraldehyde has been shown to induce a cytotoxic effect on cells. The EDC/NHS crosslinked Q-Peptide hydrogel resulted in the formation of a stable gel, which remained perfusable and viscous enough to be delivered onto a surface at a vertical orientation.

Another important characteristic in the design of an optimal wound dressing, is a controlled degradation. Resistance to hydrolytic degradation in PBS and chitosan targeting enzyme lysozyme is beneficial, as it may provide enhanced stability in vivo. The degradation profile of the hydrogel by collagenase suggests that the material is resistant to rapid degradation, but exhibits a sustained degradation with time, thereby providing continual support to the wound, similar to what one may encounter with the approved collagen-based gels.

During wound healing, there is an initial infiltration of pro-inflammatory macrophages which contributes to the clearing of necrotic tissues and cells, bacteria, and foreign debris. These macrophages then undergo a shift in polarization state to illicit downstream anti-inflammatory responses, which contribute to the migration of fibroblasts, and keratinocytes, and vascularization. Chronic wounds, however, are characterized by a prolonged state of inflammation and increased reactive oxygen species (ROS) production which prevents the wound from healing. An optimally designed biomaterial for wound healing is one which positively interacts with the native immune system to illicit a pro-healing effect.

It has previously been identified that the Q-Peptide interacts with cells through β1 integrins. Macrophages and monocytes are known to express β1 integrins. These integrins are thought to play a role in cell adhesion, localization within a wound following injury, and macrophage fusion.

The Q-Peptide hydrogel was previously shown to be effective at accelerating the rate of wound healing in a diabetic mouse model. One of the proposed modes of action was increased keratinocyte migration, resulting in rapid re-epithelialization, however, the interaction of the Q-Peptide hydrogel with the immune system has yet to be elucidated.

Traditionally, macrophages have been divided into two classifications, M(LPS), or pro-inflammatory, and M(IL-4), or anti-inflammatory macrophages. Traditionally when macrophages are polarized towards a pro-inflammatory profile, they release cytokines such as IFN-γ, IL-1β, GM-CSF, IL-6, IL-12, MCP-1, and TNF-α, whereas anti-inflammatory macrophages release IL-4, IL-10, and TGF-β. M2b macrophages are known to produce pro-inflammatory cytokines, IL-1β, IL-6, IL-12 and TNF-α in addition to anti-inflammatory cytokines. Within the context of wound healing, it has been hypothesized that in the early repair phase, wounds are inhabited with pro-inflammatory macrophages. These macrophages transition into an anti-inflammatory polarization as wound healing progresses into the later stages of repair.

The right shift in CD86 and left shift in CD206 expression, and increased cytokine production suggests a novel BMDM polarization in response to the Q-Peptide hydrogel, with the production of both pro-inflammatory and anti-inflammatory cytokines. Significantly elevated levels of classically activated, pro-inflammatory cytokines, such as IFN-γ, IL-1β, GM-CSF, IL-6, IL-12, MCP-1, and TNF-α in response to the Q-Peptide hydrogel may stimulate an early pro-inflammatory reaction within the wound site which helps to initiate the clearing of necrotic tissue and bacteria. For example, pro-inflammatory, GM-CSF, has been shown to have a pro-healing effect on chronic wounds by increasing VEGF production, and acting as a chemotactic for a number of skin-resident cells, thus supporting wound closure. Further, elevated concentrations of IL-4, IL-6, IL-10, and IL-12 can have downstream anti-inflammatory effects, such as promoting cell migration, and granulation tissue production. Therefore, the increased presence of IL-4 and other anti-inflammatory cytokines suggest a unique polarization state. Although the Q-Peptide film stimulated an increased release in immune cytokines, the concentration for some cytokines still remains less than classically M(LPS)/M(IL-4) stimulated BMDMs. More notably, the concentration of IL-6, IL-10, and MCP-1 as a result of LPS stimulation, was an order of magnitude greater than when BMDMs were cultured on the Q-Peptide film. This difference further supports a unique polarization as a result of the Q-Peptide film, in which the concentration of classical pro-inflammatory cytokines is less than LPS polarization, but there is an increase in pro-healing cytokines.

IL-2, which is not regularly released by macrophages under LPS or IL-4 stimulation, was significantly increased when BMDMs were cultured on the Q-Peptide hydrogel. Despite a high purity of differentiated monocytes (FIG. 6B), 10% of the population remains unidentified. Therefore, there is the possibility that the remaining 10% of the macrophage population, may be dendritic cells, which are similarly differentiated from monocytes in the presence of GM-CSF, and have been shown to differentiate in the presence of M-CSF. Dendritic cells are known to produce IL-2, which plays a role in T-cell expansion and activation. Therefore, it is possible that the increase in IL-2 concentration could be the result of activated dendritic cells in response to the Q-Peptide. However, skin T-cells, which are typically recruited to the wound in the days following injury, may help to fight wound infection and release a number of growth factors, such as keratinocyte growth factors (KGFs) and insulin-like growth factors (IGFs), which coordinate the recruitment of keratinocytes and other immune responses. In T-cell deficient animal models, skin wounds are plagued by a reduced rate of wound healing, and reduced expression of KGF, leading to a decreased production of extracellular matrix and granulation tissue, thus highlighting the integral role played by T-cells in wound healing. In addition to T-cells, other cells in the wound microenvironment, such as fibroblasts and keratinocytes, have been found to have IL-2 receptors. IL-2 signalling has been shown to act as a growth signal for fibroblasts, and stimulates fibroblasts to release MCP-1 and intracellular adhesion molecule (ICAM-1). Early studies observed an increase in wound strength and hydroxyproline when rats were treated systemically with IL-2, suggesting increased levels of IL-2 may result in improved wound quality, however there have been no recent applications of IL-2 for improved wound healing. An upregulation of IL-2 may contribute to an early inflammatory infiltration, while having downstream effects on fibroblasts, such as ECM production.

TGF-β can be found in 3 different isoforms, TGF-β1, 2, and 3. Despite sharing over 80% of their structure, the isoforms each have a unique function in wound healing and development. Given the popularity of TGF-β1 and its role in fibrosis, a significant amount of work has been invested in this particular TGF-β isoform, and in particular, its relationship with macrophages. Recently, TGF-β3 has gained popularity for its connection in abrogating scaring. As such, studies have recently begun to discern the role of each isoform in diseases. One such study observed an increase in the cellular localization of TGF-β2 and -β3 in macrophages in damaged skeletal tissue. They proposed that the increase in localization is the result of TGF-β2 and -β3 production by macrophages in the wounded area. Therefore, it is in fact plausible that the increase in TGF-β3 concentration is from macrophage release. The scrambled film induced a significant increase in the concentration of TGF-β1, whereas the Q-Peptide film did not, suggesting the role of the immobilized Q-Peptide in abrogating the release of the pro-fibrotic TGF-β1. In addition to being regularly used to induce fibrosis in vitro, TGF-β1 has been found to promote hypertrophic scars implicating its role in scar formation. Interestingly, the concentration of TGF-β3 was significantly increased only when the macrophages were cultured on the Q-Peptide film. TGF-β3 has been shown to be necessary and beneficial in scarless wound healing. In fact, fetal skin, which exhibits scarless healing, has been shown to have high levels of TGF-β3. However, simply increasing the concentration of TGF-β3 is insufficient, given the complexity of the wound environment. A clinical trial which treated wounds with recombinant human TGF-β3 failed to reach primary and secondary outcomes of a Phase III trial. As a result, some have hypothesized that the ratio of TGF-β3/TGF-β1 is more indicative of the likelihood of scarless healing. Therefore, an increase in the ratio of TGF-β3/TGF-β1 in BMDMs cultured with the Q-Peptide film suggests that the Q-Peptide hydrogel may support scarless healing.

The scrambled film exclusively induced a pro-inflammatory response, as seen by the increase in IL-1β, GM-CSF, IL-6, IL-12, MCP-1, and TNF-α. Given that there is no change in cytokine concentration when BMDMs are cultured on the empty collagen-chitosan film, it is possible that the inflammatory response could be the result of the EDC chemistry required to conjugate the peptide, or the presence of a short random peptide sequences whose presence could be induced at the time of injury. A number of short sequence, biomimetic peptides have been shown to induce a proinflammatory macrophage response, as seen by the increased release of pro-inflammatory cytokines. Tylotoin, a 12 amino acid peptide sequence was shown to increase the release of IL-6 and TGF-β1 from murine macrophages, and cathelicidin-NV, a 24 amino acid residue peptide promoted the increased release of MCP-1, TNF-α, vascular endothelial growth factor (VEGF), and TGF-β1. As a result, it is possible that the pro-inflammatory response observed from the scrambled film was a non-specific response to the presence of a general peptide sequence.

Moreover, the Q-Peptide only had an effect on BMDM cytokine release when immobilized to a hydrogel. This finding is consistent with our previous study where the effects of the Q-Peptide hydrogel on keratinocytes were only observed when the peptide was immobilized. During wound healing, the Q-Peptide hydrogel will only be able to induce a response on macrophages in close proximity to the wound and hydrogel treatment, and any systemic Q-Peptide, as a result of degradation, is likely to have little to no effect on systemic immune response.

The Q-Peptide has been shown to be effective not only in a diabetic mouse wound model, but also in a rat myocardial infarction model, thus supporting its potential use not only for wound repair, but whole body tissue repair following injury. Given the prevalence of an immune response following any form of injury, it is imperative in the clinical development of the Q-Peptide to elucidate its interaction with the immune system. However, it is important to highlight some of the limitations that exist within this study. This research serves only as a preliminary step in uncovering the mechanistic interaction between the Q-Peptide hydrogel and the immune system.

N. References for Example 1

1. Xiao, Y.; Reis, L. A.; Feric, N.; Knee, E. J.; Gu, J.; Cao, S.; Laschinger, C.; Londono, C.; Antolovich, J.; McGuigan, A. P.; Radisic, M., Diabetic wound regeneration using peptide-modified hydrogels to target re-epithelialization. *Proceedings of the National Academy of Sciences of the United States of America* 2016, 113 (40), E5792-E5801.
2. Radisic, M. X., Yun; Reis, Lewis; Mandla, Serena Hydrogel Composition and Associated Method of Use. 2018.
3. Reis, L. A.; Chiu, L. L. Y.; Liang, Y.; Hyunh, K.; Momen, A.; Radisic, M., A peptide-modified chitosan-collagen hydrogel for cardiac cell culture and delivery. *Acta Biomaterialia* 2012, 8 (3), 1022-1036.
4. Reis, L. A.; Chiu, L. L. Y.; Wu, J.; Feric, N.; Laschinger, C.; Momen, A.; Li, R. K.; Radisic, M., Hydrogels with integrin-binding angiopoietin-1-derived peptide, QHREDGS, for treatment of acute myocardial infarction. *Circulation: Heart Failure* 2015.
5. Caló, E.; Khutoryanskiy, V. V., Biomedical applications of hydrogels: A review of patents and commercial products. *European Polymer Journal* 2015, 65, 252-267.
6. Sood, A.; Granick, M. S.; Tomaselli, N. L., Wound Dressings and Comparative Effectiveness Data. *Advances in wound care* 2014, 3 (8), 511-529.
7. Olde Damink, L. H. H.; Dijkstra, P. J.; van Luyn, M. J. A.; van Wachem, P. B.; Nieuwenhuis, P.; Feijen, J., Cross-linking of dermal sheep collagen using a water-soluble carbodiimide. *Biomaterials* 1996, 17 (8), 765-773.
8. Delgado, L. M.; Bayon, Y.; Pandit, A.; Zeugolis, D. I., To cross-link or not to cross-link? Cross-linking associated foreign body response of collagen-based devices. *Tissue engineering. Part B, Reviews* 2015, 21 (3), 298-313.
9. Yoo, J. S.; Kim, Y. J.; Kim, S. H.; Choi, S. H., Study on genipin: a new alternative natural crosslinking agent for fixing heterograft tissue. *The Korean journal of thoracic and cardiovascular surgery* 2011, 44 (3), 197-207.
10. McDade, J. K.; Brennan-Pierce, E. P.; Ariganello, M. B.; Labow, R. S.; Michael Lee, J., Interactions of U937 macrophage-like cells with decellularized pericardial matrix materials: Influence of crosslinking treatment. *Acta Biomaterialia* 2013, 9 (7), 7191-7199.
11. MacEwan, M. R.; MacEwan, S.; Kovacs, T. R.; Batts, J., What Makes the Optimal Wound Healing Material? A Review of Current Science and Introduction of a Synthetic Nanofabricated Wound Care Scaffold. *Cureus* 2017, 9 (10), e1736-e1736.
12. Martinez, F. O.; Gordon, S., The M1 and M2 paradigm of macrophage activation: time for reassessment. *F1000prime reports* 2014, 6, 13-13.
13. Krzyszczyk, P.; Schloss, R.; Palmer, A.; Berthiaume, F., The Role of Macrophages in Acute and Chronic Wound Healing and Interventions to Promote Pro-wound Healing Phenotypes. *Front Physiol* 2018, 9.
14. Wang, L.-x.; Zhang, S.-x.; Wu, H.-j.; Rong, X.-l.; Guo, J., M2b macrophage polarization and its roles in diseases. *Journal of Leukocyte Biology* 2018, 0 (0).
15. Le, M.; Naridze, R.; Morrison, J.; Biggs, L. C.; Rhea, L.; Schutte, B. C.; Kaartinen, V.; Dunnwald, M., Transforming Growth Factor Beta 3 Is Required for Excisional Wound Repair In Vivo. *PLoS ONE* 2012, 7 (10), e48040-e48040.
16. Occleston, N. L.; O'Kane, S.; Laverty, H. G.; Cooper, M.; Fairlamb, D.; Mason, T.; Bush, J. A.; Ferguson, M. W. J., Discovery and development of avotermin (recombinant human transforming growth factor beta 3): A new class of prophylactic therapeutic for the improvement of scarring. *Wound Repair and Regeneration* 2011, 19 (s1), s38-s48.
17. Tang, J.; Liu, H.; Gao, C.; Mu, L.; Yang, S.; Rong, M.; Zhang, Z.; Liu, J.; Ding, Q.; Lai, R., A small peptide with potential ability to promote wound healing. *PloS one* 2014, 9 (3), e92082-e92082.
18. Cao, X.; Wang, Y.; Wu, C.; Li, X.; Fu, Z.; Yang, M.; Bian, W.; Wang, S.; Song, Y.; Tang, J.; Yang, X., Cathelicidin-OA1, a novel antioxidant peptide identified from an amphibian, accelerates skin wound healing. *Scientific reports* 2018, 8 (1), 943-943.
19. Niyonsaba, F.; Ushio, H.; Nakano, N.; Ng, W.; Sayama, K.; Hashimoto, K.; Nagaoka, I.; Okumura, K.; Ogawa, H., Antimicrobial Peptides Human β-Defensins Stimulate Epidermal Keratinocyte Migration, Proliferation and Production of Proinflammatory Cytokines and Chemokines. *Journal of Investigative Dermatology* 2007, 127 (3), 594-604.

The invention claimed is:

1. A method of inducing a polarization state of a macrophage, the method comprising contacting the macrophage with a formulation, wherein the formulation comprises a peptide that comprises the amino acid sequence QHREDGS (SEQ ID NO: 1) cross-linked to a carrier;

wherein the carrier is selected from hydrogel, glycerol, propylene glycol, chitosan, alginate, agarose, polyether, polyester, methylcellulose, hyaluronan, collagen, laminin, fibronectin, vitronectin, poly-1-lysine, a proteoglycan, fibrin glue, a gel made by decellularization of an engineered or natural tissue, polyglycolic acid (PGA), polylactic acid (PLA), a combination of PGA and PLA, PLGA, poly ε-caprolactone, polyvinyl alcohol (PVA), polyethylene glycol (PEG), methyl methacrylate, poly(methyl methacrylate) (PMMA), poly(-hydroxyethyl methacrylate) (PolyHEMA), poly (glycerol sebacate), a self-assembling peptide hydrogel, AcN-RARADADARARADADA-CNH (SEQ ID NO: 2), polyurethane, poly(isopropylacrylamide), poly (N-isopropylacrylamide), and a combination thereof.

2. The method of claim 1, wherein the polarization state is characterized by an increase in release of a pro-inflammatory cytokine and an increase in anti-inflammatory cytokine production by the macrophage relative to a macrophage that has not been contacted with the formulation.

3. The method of claim 2, wherein the pro-inflammatory cytokine is selected from IFN-γ, IL-1 fβ, GM-CSF, IL-12, and a combination thereof.

4. The method of claim 2, wherein the anti-inflammatory cytokine is selected from IL-4, IL-10, TGFβ1, TGFβ3, and a combination thereof.

5. The method of claim 1, wherein the polarization state is characterized by an increase in the ratio of TGF-β3/TGFβ1 released by the macrophage relative to a macrophage that has not been contacted with the formulation.

6. The method of claim 1, wherein the contacting step is performed in vitro.

7. The method of claim 1, wherein the contacting step is performed in vivo.

8. The method of claim 7, wherein the contacting step is performed on a human.

9. The method of claim 1, wherein the formulation is in the form of a hydrogel.

10. The method of claim 1, wherein the formulation is in the form of a gel, a tincture, a cream, an ointment, a lotion, or an aerosol spray.

11. The method of claim 1, wherein the formulation is delivered on a patch or a bandage.

12. The method of claim 1, wherein the polarization state is characterized by a decrease in expression level of CD206 on the macrophage relative to a macrophage that has not been contacted with the formulation.

13. The method of claim 1, wherein the carrier is the hydrogel, and wherein the hydrogel is a cross-linked hydrogel and comprises chitosan and collagen.

* * * * *

UNITED STATES PATENT AND TRADEMARK OFFICE
CERTIFICATE OF CORRECTION

| | | |
|---|---|---|
| PATENT NO. | : 11,766,469 B2 | Page 1 of 1 |
| APPLICATION NO. | : 17/086786 | |
| DATED | : September 26, 2023 | |
| INVENTOR(S) | : Serena Mandla and Milica Radisic | |

It is certified that error appears in the above-identified patent and that said Letters Patent is hereby corrected as shown below:

In the Claims

In Column 35, Line 41 (Claim 3): "cytokine is selected from IFN-y, IL-1 fß, GM-CSF, IL-12" should read --cytokine is selected from IFN-y, IL-1ß, GM-CSF, IL-12--.

Signed and Sealed this
Fifth Day of December, 2023

Katherine Kelly Vidal
*Director of the United States Patent and Trademark Office*

SEQUENCE LISTING

<160> NUMBER OF SEQ ID NOS: 22

<210> SEQ ID NO 1
<211> LENGTH: 7
<212> TYPE: PRT
<213> ORGANISM: Artificial Sequence -continued

```
<220> FEATURE:
<223> OTHER INFORMATION: Synthetic Polypeptide

<400> SEQUENCE: 1

Gln His Arg Glu Asp Gly Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 2

Arg Ala Arg Ala Asp Ala Asp Ala Arg Ala Arg Ala Asp Ala Asp Ala
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 3

Arg Glu Asp Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 4

Arg Leu Asp Gly
1

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

Arg Glu Asp Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 6

Arg Leu Asp Gly Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

His Arg Glu Asp Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

His Arg Leu Asp Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 9

His Arg Glu Asp Gly Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

His Arg Leu Asp Gly Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

Gln His Arg Glu Asp Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 12

Gln His Arg Leu Asp Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 13

Gln His Arg Glu Asp Val Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 14

Gln His Arg Glu Asp Gly Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 15

Gln His Arg Leu Asp Gly Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 16

Lys Arg Leu Asp Gly Ser
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 17

Gln His Arg Glu Asp Gly Ser Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Polypeptide
```

```
<400> SEQUENCE: 18

Gln His Arg Leu Asp Gly Ser Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 19

Gln His Arg Leu Asp Gly Ser Leu Asp
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 20

Gln His Arg Glu Asp Gly Ser Leu Asp
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa may be Gln, Thr, Ser or Asn or may be
      absent
<220> FEATURE:
<221> NAME/KEY: MISC_FEATURE
<222> LOCATION: (2)..(2)
<223> OTHER INFORMATION: Xaa may be His, Arg, Lys or may be absent
<220> FEATURE:
<221> NAME/KEY: MISC_FEATURE
<222> LOCATION: (3)..(3)
<223> OTHER INFORMATION: Xaa may be Glu, Thr, Ile, His, Lys, Gln, Tyr,
      Val or Lys
<220> FEATURE:
<221> NAME/KEY: MISC_FEATURE
<222> LOCATION: (4)..(4)
<223> OTHER INFORMATION: Xaa may be Gly or Val
<220> FEATURE:
<221> NAME/KEY: MISC_FEATURE
<222> LOCATION: (5)..(5)
<223> OTHER INFORMATION: Xaa may be Ser, Thr, Asp, Ile, Gly or may be
      absent
<220> FEATURE:
<221> NAME/KEY: MISC_FEATURE
<222> LOCATION: (6)..(6)
<223> OTHER INFORMATION: Xaa may be Leu, Val, Gln, Gly, Ile, Ser or may
      be absent
<220> FEATURE:
<221> NAME/KEY: MISC_FEATURE
<222> LOCATION: (7)..(7)
<223> OTHER INFORMATION: Xaa may be Asp, Asn, Val, Lys or may be absent

<400> SEQUENCE: 21

Xaa Xaa Xaa Xaa Xaa Xaa Xaa
1               5
```

```
<210> SEQ ID NO 22
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 22

Asp Gly Gln Glu Ser His Arg
1               5
```